United States Patent
Eli

(10) Patent No.: US 10,702,366 B2
(45) Date of Patent: Jul. 7, 2020

(54) INTRA-AORTIC EMBOLI PROTECTION FILTER DEVICE

(71) Applicant: FILTERLEX MEDICAL LTD., Yokneam (IL)

(72) Inventor: Sigalit Eli, Tel-Aviv (IL)

(73) Assignee: FILTERLEX MEDICAL LTD., Yokneam (IL)

( * ) Notice: Subject to any disclaimer, the term of this patent is extended or adjusted under 35 U.S.C. 154(b) by 311 days.

(21) Appl. No.: 15/757,735

(22) PCT Filed: Sep. 7, 2016

(86) PCT No.: PCT/IL2016/050992
§ 371 (c)(1),
(2) Date: Mar. 6, 2018

(87) PCT Pub. No.: WO2017/042808
PCT Pub. Date: Mar. 16, 2017

(65) Prior Publication Data
US 2019/0000604 A1 Jan. 3, 2019

Related U.S. Application Data

(60) Provisional application No. 62/215,075, filed on Sep. 7, 2015.

(51) Int. Cl.
*A61F 2/01* (2006.01)

(52) U.S. Cl.
CPC .............. *A61F 2/01* (2013.01); *A61F 2/013* (2013.01); *A61F 2002/011* (2013.01);
(Continued)

(58) Field of Classification Search
CPC ...... A61F 2/01; A61F 2/013; A61F 2002/001; A61F 2002/016; A61F 2002/018;
(Continued)

(56) References Cited

U.S. PATENT DOCUMENTS

| 2002/0095169 A1 | 7/2002 | Maitland et al. |
| 2003/0100919 A1 | 5/2003 | Hopkins et al. |

(Continued)

FOREIGN PATENT DOCUMENTS

| WO | 2013082555 | 6/2013 |
| WO | 2015009655 | 1/2015 |

(Continued)

OTHER PUBLICATIONS

International Search Report PCT/IL2016/050992 Completed Jan. 2, 2017; dated Jan. 3, 2017 10 pages.

(Continued)

*Primary Examiner* — Erich G Herbermann
(74) *Attorney, Agent, or Firm* — The Roy Gross Law Frim, LLC; Roy Gross

(57) ABSTRACT

An embolic protection device including a porous deflector screen including a filter, arranged to expand and to conform to a wall of the aortic arch covering entrances to arteries branching from an aorta, an emboli collector including a cylinder arranged to expand and to lie along walls of a descending aorta, pushing against walls of the descending aorta and anchoring the porous deflector screen, and a connecting portion for connecting the porous deflector screen and the emboli collector, arranged to push the porous deflector screen against a wall of the aortic arch while anchoring against the emboli collector. Related apparatus and methods are also described.

19 Claims, 18 Drawing Sheets

(52) U.S. Cl.
CPC ... *A61F 2002/016* (2013.01); *A61F 2002/018* (2013.01); *A61F 2210/0014* (2013.01); *A61F 2220/0025* (2013.01); *A61F 2230/0006* (2013.01); *A61F 2230/0019* (2013.01); *A61F 2230/0023* (2013.01); *A61F 2230/0069* (2013.01); *A61F 2230/0095* (2013.01); *A61F 2230/0097* (2013.01); *A61F 2250/0067* (2013.01); *A61F 2250/0098* (2013.01)

(58) Field of Classification Search
CPC ...... A61F 2210/0014; A61F 2220/0025; A61F 2230/0006; A61F 2230/0019; A61F 2230/0023; A61F 2230/0069; A61F 2230/0095; A61F 2230/0097; A61F 2230/0008; A61F 2230/0067; A61F 2250/0067; A61F 2250/0098; A61F 6/225
USPC .............. 606/114–115, 200; 623/1.16, 1.35; 604/528; 600/585
See application file for complete search history.

(56) References Cited

U.S. PATENT DOCUMENTS

| | | | |
|---|---|---|---|
| 2006/0161241 A1* | 7/2006 | Barbut | A61F 2/013 623/1.15 |
| 2014/0005540 A1 | 1/2014 | Merhi | |
| 2014/0172006 A1 | 6/2014 | Stack et al. | |
| 2014/0243881 A1 | 8/2014 | Lees et al. | |

FOREIGN PATENT DOCUMENTS

| | | |
|---|---|---|
| WO | 2015061269 A1 | 4/2015 |
| WO | 2015104645 A2 | 7/2015 |

OTHER PUBLICATIONS

Written Opinion of the International Searching Authority PCT/IL2016/050992 dated Jan. 3, 2017 8 pages.

* cited by examiner

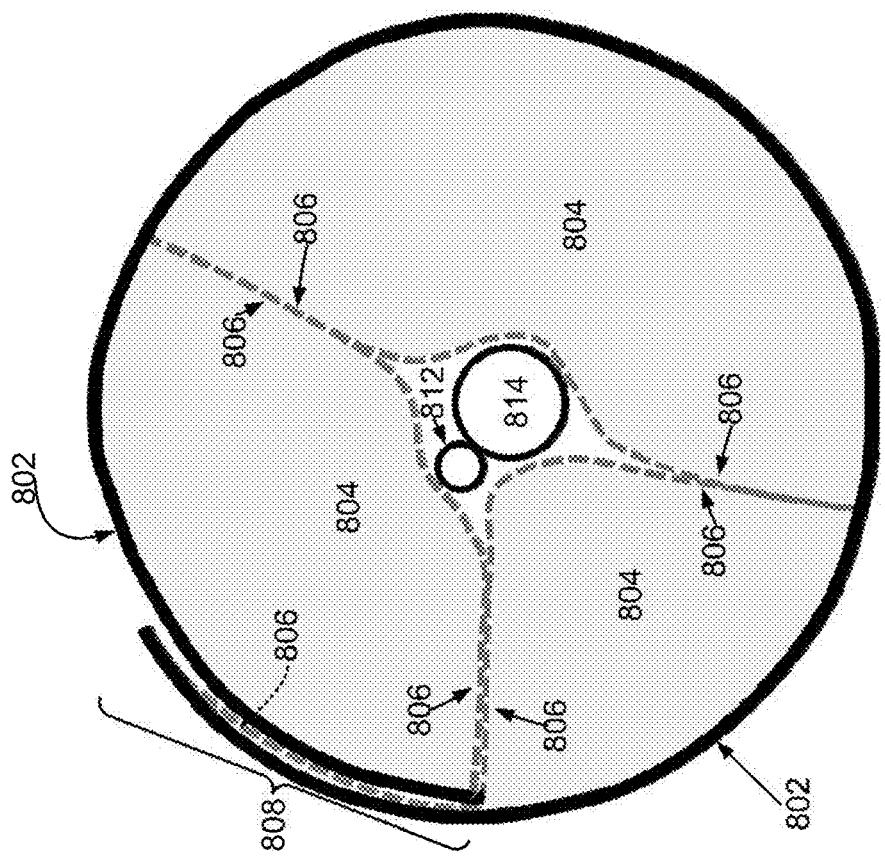
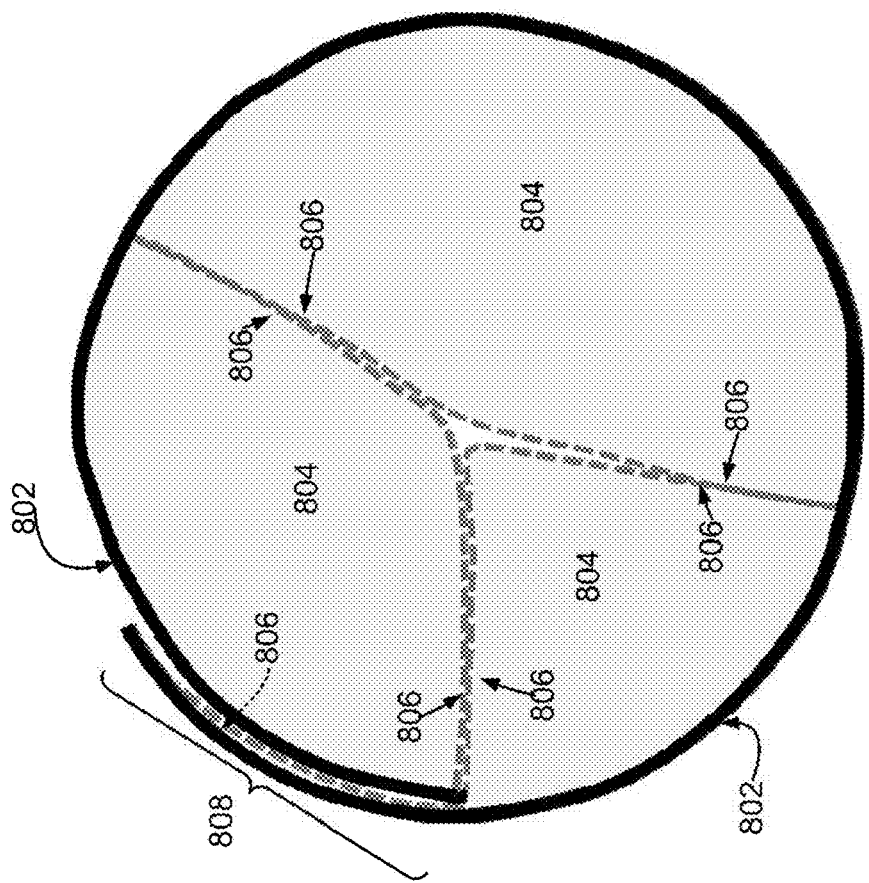
FIGURE 8B
FIGURE 8A

```
┌─────────────────────────────────────────────────────────────┐
│     PROVIDE A DEVICE WITH A DEFLECTOR SCREEN WHICH INCLUDES  │
│       A FILTER, ARRANGED TO EXPAND AND TO COVER ENTRANCES    │
│     TO ARTERIES BRANCHING FROM AN AORTA; AN EMBOLI COLLECTOR │
│      WHICH INCLUDES AN EXPANDABLE SHAPE ARRANGED TO EXPAND   │─── 912
│       AND TO PUSH AGAINST WALLS OF THE DESCENDING THORACIC   │
│         AORTA FOR ANCHORING THE DEFLECTOR SCREEN; AND A      │
│           CONNECTING PORTION FOR CONNECTING THE SCREEN       │
│                         AND THE COLLECTOR                    │
└─────────────────────────────────────────────────────────────┘
                                  │
                                  ▼
┌─────────────────────────────────────────────────────────────┐
│    INSERT THE DEVICE VIA A CATHETER INTO AN AORTA, PLACING THE│
│      DEFLECTOR SCREEN AT THE AORTIC ARCH, THE FILTER OF THE  │
│    DEFLECTOR SCREEN BLOCKING EXITS TO ARTERIES BRANCHING OFF │─── 914
│        THE AORTIC ARCH, AND THE EMBOLI COLLECTOR AT THE      │
│      DESCENDING THORACIC AORTA AND UNFURLED TO LIE ALONG     │
│             WALLS OF THE DESCENDING THORACIC AORTA           │
└─────────────────────────────────────────────────────────────┘
```

FIGURE 9A

PROVIDE A DEVICE WITH AN DEFLECTOR SCREEN WHICH INCLUDES A FILTER, ARRANGED FOR PLACING IN AN AORTIC ARCH, AN EMBOLI COLLECTOR WHICH INCLUDES A FILTER POCKET, AND A CONNECTING PORTION FOR CONNECTING SAID DEFLECTOR SCREEN AND SAID EMBOLI COLLECTOR ←—902

INSERT SAID DEVICE VIA A CATHETER INTO AN AORTA SO THAT THE UPSTREAM PORTION IS PLACED AT THE AORTIC ARCH, THE FILTER BLOCKING EXITS TO ARTERIES BRANCHING OFF SAID AORTIC ARCH AND THE EMBOLI COLLECTOR IS PLACED AT THE DESCENDING THORACIC AORTA AND OPENED TO LIE ALONG WALLS OF THE DESCENDING THORACIC AORTA ←—904

FIGURE 9B

INTRA-AORTIC EMBOLI PROTECTION FILTER DEVICE

CROSS REFERENCE TO RELATED APPLICATIONS

This application is a National Phase of PCT Patent Application No. PCT/IL2016/050992 having International filing date of Sep. 7, 2016, which claims the benefit of priority of U.S. Patent Application No. 62/215,075 filed on Sep. 7, 2015 entitled INTRA-AORTIC EMBOLI PROTECTION FILTER DEVICE. The contents of the above applications are all incorporated herein by reference as if fully set forth herein in their entirety.

FIELD AND BACKGROUND OF THE INVENTION

The present invention, in some embodiments thereof, relates to the field of intra-aortic devices.

In Transcatheter Aortic-Valve Implantation and/or Replacement (TAVI and TAVR, respectively), a catheter-based delivery system and compressed/crimped prosthetic valve may be inserted through one of the arteries and advanced to the aortic root. After careful positioning of the device in the native aortic valve, the new prosthetic valve may be deployed and may immediately function as a new aortic valve.

In on-pump procedures, heart-lung machine procedures, such as aortic valve replacement (SAVR), mitral valve replacement or repair (MVR), coronary artery bypass grafts (CABG) and other cardiac surgeries, the patient may be put on a cardiopulmonary bypass pump, and after cardiopulmonary bypass pump cross-clamp release.

The foregoing examples of the related art and limitations related therewith are intended to be illustrative and not exclusive. Other limitations of the related art will become apparent to those of skill in the art upon a reading of the specification and a study of the figures.

SUMMARY OF THE INVENTION

An aspect of some embodiments of the invention includes an intra-aortic emboli protection filter apparatus and methods for deflecting and/or capturing and/or removal of emboli particles dislodged into the blood during various cardiac interventional procedures.

An aspect of some embodiments of the invention includes a device which includes a filter-covered collapsible wire structure with one or more cross luminal element such as filter flap(s) or pocket(s) for preventing emboli particles from migrating into certain areas of the anatomy. In some embodiments, blood flow through the cross luminal elements pushes the edges of the filter to block the lumen, thereby filtering the entire cross section of the lumen. In some embodiments the device is optionally placed downstream from the aortic valve to deflect particles toward the descending aorta to capturing filter flap(s) or pocket(s). In some embodiments the device protects the walls of the aorta from the valve delivery system/other devices used in the procedure. In some embodiments the device upstream end is optionally placed in the aortic arch and the device downstream end in the descending aorta. In some embodiments the device is collapsible and can be deployed and removed using a catheter-based delivery system. In some embodiments capturing emboli particles includes using two or more adjoined filter pockets connected to the downstream part of the device to capture the emboli particles flowing downstream. In some embodiments removing emboli particles includes removing the device together with the emboli particles captured in the filter pockets.

The term "filter", as referred to herein, may relate to a porous sheet or a porous body of material, which serves for filtering blood and preventing emboli from passing through it while allowing blood without emboli, or at least without emboli larger than the pore size, to pass through the filter. One example of a filter is a mesh—a woven, knit, or knotted material, such as a mesh made of suitably arranged nitinol wires. Another example of a filter is a polymeric membrane having holes of such a size and density preventing emboli from passing therethrough. Such polymeric membrane may be taut over a relatively rigid frame. The membrane may have a uniform or a variable thickness in the range of 0.05 mm to 0.25 mm, as one example. Other thicknesses are also intended herein.

Generally, it is intended that the term "filter" covers any material with holes, whether evenly or unevenly spaced, which can serve for filtering blood and preventing emboli from passing through it while allowing blood without emboli, or at least without emboli larger than the pore size, to pass through the filter.

The terms "upstream" and "downstream" are used throughout the present specification and claims based on a direction of blood flow in a patient's body.

As using herein, the terms "conform", "conforming", and the like mean that two or more objects may have identical or similar shapes. For example, a medical device or a portion thereof said to conform to a certain anatomic structure, has a shape identical or similar to that of the anatomic structure.

According to an aspect of some embodiments of the present invention there is provided an embolic protection device comprising a porous deflector screen comprising a filter shaped as curved cylinder portion when the embolic protection device is in an expanded configuration, where the porous deflector screen is configured to expand and to conform to a wall of the aortic arch, covering entrances to arteries branching from the superior wall of the aortic arch. The embolic protection device comprises an emboli collector shaped as a cylinder when the embolic protection device is in the expanded configuration, where the emboli collector is configured to expand and to lie along walls of the descending aorta, pushing against walls of the descending aorta and anchoring the porous deflector screen, where the emboli collector comprises one or more elongated filter pocket having an opening directed towards the porous deflector screen. The concavity of the one or more elongated filter pocket is directed opposite to the opening. When the embolic protection device is in an expanded configuration, the one or more elongated filter pocket spans at least partway a cylindrical volume, with the length of the one or more elongated filter pocket being along the height of the cylindrical volume. The embolic protection device comprises a connecting portion for connecting the porous deflector screen and the emboli collector, configured to push the porous deflector screen against the superior wall of the aortic arch while anchoring against the emboli collector.

Optionally, the porous deflector screen comprises an expandable frame.

Optionally, the emboli collector comprises a filter.

An aspect of some embodiments of the invention includes a filter sized to expand and to lie along walls of a descending aorta, the filter comprising holes designed to filter blood through and block emboli.

Optionally, the porous deflector screen comprises an expandable frame.

Optionally, the connecting portion is longer than 2 centimeters.

Optionally, the connecting portion is longer than 7 centimeters.

Optionally, the connecting portion is shaped to expand to the shape of a curved cylinder portion.

Optionally, the one or more elongated filter pocket comprises a plurality of elongated filter pockets disposed in parallel.

Optionally, the emboli collector is shaped to expand to a cylindrical shape.

Optionally, the emboli collector comprises support struts.

Optionally, the emboli collector comprises an expandable stent-like shape.

Optionally, the one or more elongated filter pocket comprises a frame at an edge of the opening.

Optionally, one or more radio-opaque marker is attached to the opening.

Optionally, the device comprises one or more radio-opaque marker.

Optionally, the one or more radio-opaque marker is attached to the porous deflector screen.

Optionally, the one or more radio-opaque marker is attached to the emboli collector.

Optionally, the one or more radio-opaque marker is attached to the connecting portion.

Optionally, at least some of the plurality of elongated filter pockets are at least partially directly attached to each other.

Optionally, the one or more elongated filter pocket comprises a mechanism for closing the opening.

Optionally, the device further includes radio-opaque markers for distinguishing when the one or more elongated filter pocket is open and when the one or more elongated filter pocket is closed.

Optionally, the mechanism comprises a cord for drawing closed the opening when the cord is pulled.

Optionally, one or more downstream end of one or more of the plurality of elongated filter pockets is at a different distance from an upstream end of the emboli collector than one or more other end of one or more other of the plurality of pockets.

Optionally, the downstream ends of the plurality of elongated filter pockets are at a same distance from an upstream end of the emboli collector.

Optionally, the plurality of elongated filter pockets have different sized pocket openings.

Optionally, one or more of the plurality of elongated filter pockets has a different width than one or more other of the plurality of elongated filter pockets.

Optionally, the emboli collector is structured to overlap by at least 10% of a circumference of the descending aorta.

Optionally, the emboli collector is structured to overlap by at least 30% of a circumference of the descending aorta.

Optionally, the surface of the emboli collector is structured to overlap by at least 50% of a circumference of the descending aorta.

Optionally, the emboli collector further comprises support struts.

Optionally, the emboli collector further comprises stent-like support struts.

Optionally, the emboli collector further comprises a frame.

Optionally, the filter of the porous deflector screen further comprises support struts attached to the filter.

Optionally, the filter of the porous deflector screen further comprises a frame attached to a circumference of the filter.

Optionally, the emboli collector further comprises a wire arranged to extend downstream.

Optionally, the wire further comprises a ring.

Optionally, the wire further comprises a radio-opaque marker at its downstream end.

Optionally, the porous deflector screen is arranged to anchor against walls of the aortic arch by applying radial force to the walls of the aortic arch.

Optionally, the emboli collector is arranged to anchor against walls of the descending aorta by applying radial force to the walls of the descending aorta.

According to an aspect of some embodiments of the present invention there is provided an embolic protection device comprising a surface arranged to expand and to lie along walls of a blood vessel, pushing against walls of the blood vessel. The embolic protection device further comprises a plurality of filter pockets attached to the surface, each one of the filter pockets arranged to extend at least partway across a lumen of the blood vessel, for trapping emboli flowing downstream, where the plurality of pockets are arranged to enable a surgical tool to pass through the lumen between the filter pockets.

According to an aspect of some embodiments of the present invention there is provided a method for protecting a patient against flow of emboli from an aorta to branching arteries, the method comprising providing a device and inserting the device via a catheter into an aorta. The device comprises a porous deflector screen comprising a filter shaped as curved cylinder portion when the embolic protection device is in an expanded configuration, where the porous deflector screen is configured to conform to a superior wall of the aortic arch, covering entrances to arteries branching from the aorta.

The device comprises an emboli collector shaped as a cylinder when the embolic protection device is in the expanded configuration, where the emboli collector is configured to expand and to lie along walls of the descending aorta, pushing against walls of the descending aorta and anchoring the porous deflector screen, where the emboli collector comprises one or more elongated filter pocket having an opening directed towards the porous deflector screen. The concavity of the one or more elongated filter pocket is directed opposite to the opening. When the embolic protection device is in an expanded configuration, the one or more elongated filter pocket spans at least partway a cylindrical volume, with the length of the one or more elongated filter pocket being along the height of the cylindrical volume. The device comprises a connecting portion for connecting the porous deflector screen and the emboli collector, configured to push the porous deflector screen against the superior wall of the aortic arch while anchoring against the emboli collector. The porous deflector screen is placed at the aortic arch, the filter of the porous deflector screen blocking exits to arteries branching superiorly off the aortic arch. The emboli collector is placed at the descending aorta and unfurled so the surface lies along walls of the descending aorta.

Optionally, the method further comprises using a catheter to remove the device from the aorta.

Optionally, the method further comprises closing the opening of the one or more elongated filter pocket prior to removing the device from the aorta.

Optionally, the method further comprises closing the opening of the one or more elongated filter pocket by pulling a cord for drawing closed the opening prior to removing the device from the aorta.

Optionally, the method further comprises performing a procedure on a heart of the patient by passing a surgical tool through the emboli collector of the device, next to the filter pocket.

Optionally, the one or more elongated filter pocket comprises a plurality of elongated filter pockets, and further comprising performing a procedure on a heart of the patient by passing a surgical tool through the emboli collector of the device, between the plurality of elongated filter pockets.

Optionally, the method further comprises, following the inserting, performing an on-pump cardiac operation on a heart of the patient.

Optionally, the method further comprises leaving the device within the aorta following conclusion of the on-pump cardiac operation.

Optionally, the method further comprises using a catheter to remove the device from the aorta.

According to an aspect of some embodiments of the present invention there is provided a method for distinguishing between an open state and a closed state of a flexible pocket implanted in a patient. The method comprises using at least two radio-opaque markers attached to the pocket. The method comprises imaging the at least two radio-opaque markers. The method comprises determining whether the flexible pocket is open or closed based, at least in part, on a distance between the radio-opaque markers.

According to an aspect of some embodiments of the present invention there is provided an embolic protection device comprising an upstream portion comprising a filter, arranged to expand and to conform to a wall of the aortic arch covering entrances to arteries branching from an aortic arch. The device comprises a downstream portion comprising an expandable shape arranged to expand and to lie along walls of a descending aorta, pushing against walls of the descending aorta and at least partially anchor the embolic protection device. The device comprises a filter pocket attached to the expandable shape of the downstream portion, arranged to extend from the walls of the descending aorta at least partway across a lumen of the descending aorta, for trapping emboli flowing downstream. The device comprises a connecting portion for connecting the upstream portion and the downstream portion, arranged to push the upstream portion against walls of the aortic arch while anchoring against the downstream portion.

According to an aspect of some embodiments of the present invention there is provided an embolic protection device comprising an upstream portion comprising a filter, arranged to expand and to conform to a wall of the aortic arch covering entrances to arteries branching from an aorta. The device comprises a downstream portion comprising a surface arranged to expand and to lie along walls of a descending aorta, pushing against walls of the descending aorta and anchoring the upstream portion. The device comprises a connecting portion for connecting the upstream portion and the downstream portion, arranged to push the upstream portion against a wall of the aortic arch while anchoring against the downstream portion.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 8A is a simplified cross-sectional illustration of an emboli collector of an intra-aortic emboli protection filter as deployed in an aorta according to an example embodiment of the invention;

FIG. 8B is a simplified cross-sectional illustration of an emboli collector of an intra-aortic emboli protection filter as deployed in an aorta similar to the drawing in FIG. 8A;

FIG. 9A is a simplified flow chart illustration of a method for protecting a patient against flow of emboli from an aorta to branching arteries according to an example embodiment of the invention;

FIG. 9B is a simplified flow chart illustration of a method for protecting a patient against flow of emboli from an aorta to branching arteries according to an example embodiment of the invention;

DETAILED DESCRIPTION

Figure 1:
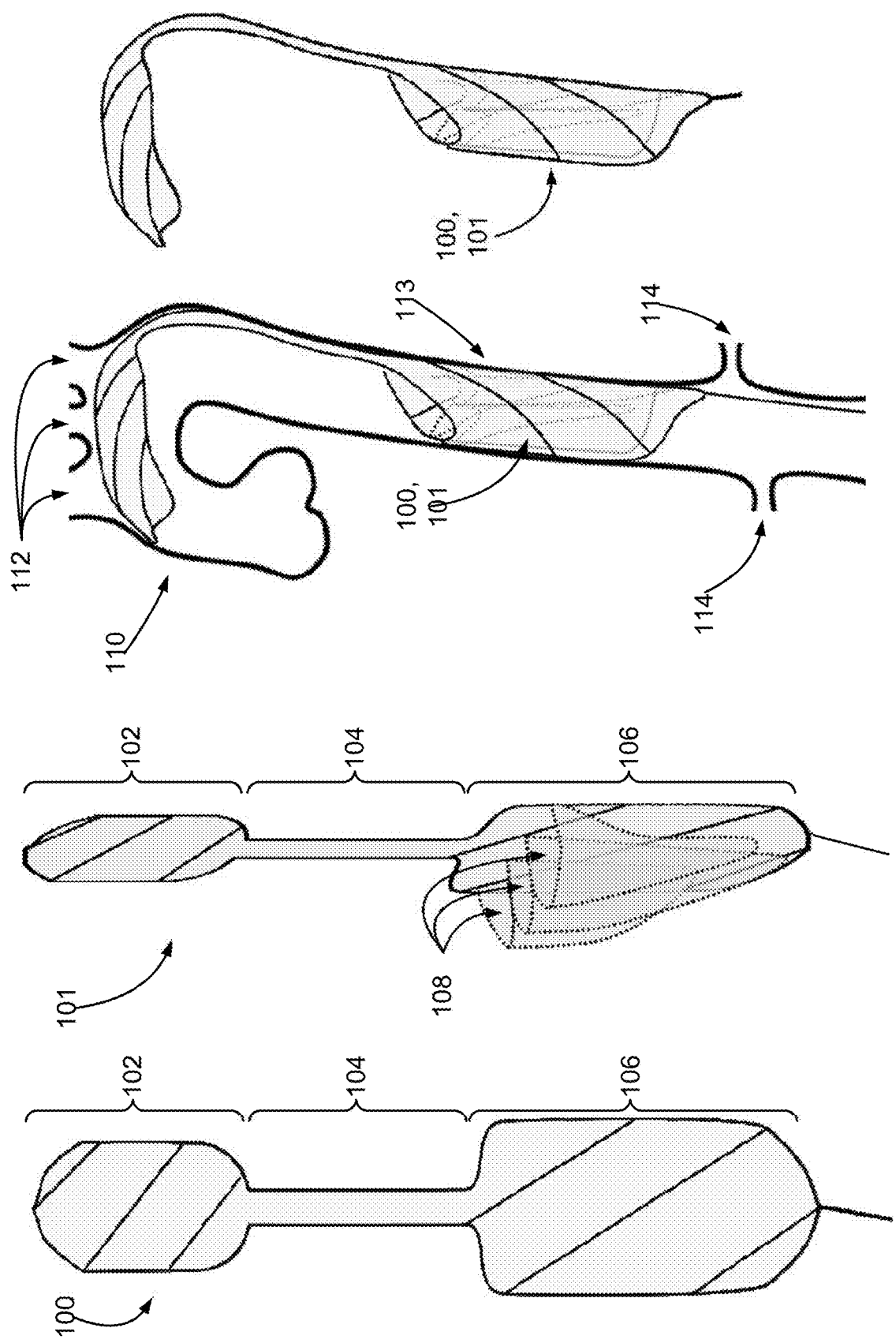
FIG. 1A is a simplified illustration of an intra-aortic emboli protection filter according to an example embodiment of the invention.
FIG. 1B is a simplified illustration of an intra-aortic emboli protection filter according to an example embodiment of the invention.
FIG. 1C is a simplified illustration of the intra-aortic emboli protection filter of FIG. 1A or 1B deployed in an aorta according to an example embodiment of the invention.
FIG. 1D is a simplified illustration of the intra-aortic emboli protection filter of FIG. 1A or 1B as deployed in the aorta, depicting only the deployed intra-aortic emboli protection filter and not the aorta, according to an example embodiment of the invention.

The present invention, in some embodiments thereof, relates to an intra-aortic device and methods of using the device, and, more particularly, but not exclusively, to an intra-aortic emboli protection filter and methods of using the filter in various cardiac procedures.

The device with three portions—a porous deflector screen, a connecting portion, and an emboli collector portion—may prevent particles in the blood stream from entering the arteries exiting the aortic arch with the porous deflector screen, and capture them later downstream with the emboli collector. The porous deflector screen may be a perforated material, such as a filter, a mesh, a porous membrane, and the like, that may cover the opening(s) to one or more of the arteries branching from the superior wall of the aortic arch.

The porous deflector screen may be structured as an elongated surface, curved in two approximately perpendicular directions, with both directions of the same orientation, such as most points of the surface having curvatures of the same sign. Therefore, most points on the elongated surface are geometric elliptical points. The first direction has a smaller diameter of curvature along the shorter dimension of the elongated surface, such as following the tubular cross section perimeter of the aorta at each point along the aorta. The second direction has a larger diameter of curvature along the longer dimension of the elongated surface, such as following the path of the aortic arch, such as the longitudinal axis of the aortic lumen. Thus, the elongated surface may be considered bi-concave and may have a shape resembling a curved cylinder portion that conforms to the shape of the aortic arch. As used herein, the term curved cylinder portion means the bi-concave elongated surface described above.

The connecting portion may have a length between a few millimeters and up to 30 centimeters, and may be elastic to press the porous deflector screen over the openings of the arteries branching from the aortic arch. For example, the connecting portion presses the porous deflector screen against the aortic arch with a pressure of 0.1 kilopascal (KPa), 1 KPa, 2 KPa, 5 KPa, 10 KPa, 20 KPa, 50 KPa, and the like. Optionally, the connecting portion presses the porous deflector screen against the aortic arch with a pressure of between 0.01 KPa and 10 megapascal (MPa). The emboli collector portion captures the particles in the blood stream, and retains them within the filter for removal from the patient's body. This prevents the particles migrating to other body parts during a cardiac procedure from causing harm to a patient, such as a stroke, embolism, and the like.

Optionally, the device or portions thereof form a protective layer along the inner perimeter of the aorta (when in the expanded configuration) for protecting the aorta from damage by an interventional instrument, such as a catheter, wire, valve delivery system, and/or the like, when entering and/or moving along the aorta. For example, the material of the device or those portions thereof may have a low coefficient of friction, or be coated with a low coefficient of friction material, to facilitate the surgical instrument in moving freely along the aortic arch. For example, the material is a biocompatible metal to prevent friction of an interventional instrument with the aorta wall. For example, the material is a biocompatible plastic or polymer to prevent friction of an interventional instrument with the aorta wall and to facilitate the interventional instrument in moving freely and smoothly along the aorta.

The device may have a collapsed configuration and an expanded configuration. When the device is being inserted into the descending aorta and aortic arch, it may be in the collapsed configuration, and have a flexible elongated shape, approximately cylindrical, with a length between 5 and 50 centimeters and of a diameter between 1 and 20 millimeters, such as configured to be deployed with a minimally invasive surgical tool.

When in the expanded configuration:

The elongated connecting portion has a length of between 1 centimeter and 30 centimeters.

Diameters of the elongated filter pockets are between 0.2 centimeter and 5 centimeters. The pockets, when expanded, cover at least 5 percent of the volume of the lumen of the descending aorta, such as the volume of a cylinder between 1 and 1000 centiliters, and the pockets cover at least 20% of the cross sectional area of the descending aorta, up to 100% thereof The diameter of curvature along the first direction of the porous deflector screen is between 5 millimeters and 100 millimeters.

The diameter of curvature along the second direction of the porous deflector screen is between 1 centimeter and 30 centimeters.

The arch along the porous deflector screen's short dimension (such as along the perimeter of a cross section of the aorta) may span between 20 degrees and 360 degrees.

The porous deflector screen's long dimension covers between 10 and 200 degrees of the aorta's arch annular circumference (along the aortic arch).

Embodiments of the devices described herein, when inserted into an aortic arch prior to a medical procedure may deflect emboli from entering arteries along the aortic arch and collect them later in the descending aorta using the filter pockets.

For example, medical procedures on a heart may cause particulate emboli to be released to the bloodstream. The particles may migrate to the brain and/or to other vital organs and cause significant damage to these organs.

For example, during TAVI/TAVR valve delivery, manipulation and deployment, calcium particles may be dislodged from the stenotic native aortic valve and the surrounding vasculature to the vascular system. Together with aortic valve leaflets, collagenous and isolated thrombus, these particles might migrate to the brain and to other vital organs and cause significant damage to these organs.

For example, particulate emboli are released to the bloodstream; these particles might migrate to the brain and to other vital organs and cause significant damage to these organs.

Some example embodiments of cardiac procedures which may potentially benefit from using an intra-aortic emboli protection device and methods as described herein include trans-catheter procedures such as trans-catheter aortic valve implantation or replacement (TAVI/TAVR), atrial fibrillation ablation, left atrial appendage closure, and mitral valve repair and replacement; as well as non-trans-catheter procedures such as various on-pump and not on-pump cardiac procedures.

An aspect of some embodiments of the invention includes an intra-aortic emboli protection filter apparatus and methods for deflecting and/or capturing and/or removal of emboli particles during various cardiac interventional procedures.

An aspect of some embodiments of the invention includes a device with an emboli protection filter placed in an aortic arch for filtering blood to arteries exiting the aortic arch and/or deflecting emboli downstream along the aorta, and an anchor for the filter placed further downstream, in the descending aorta, the aortic arch filter optionally connected to the anchor by a connecting portion for pushing the aortic arch filter against a wall of the aortic arch.

In some embodiments, the anchor includes a cross luminal filter or filters extending across the aorta for trapping emboli and preventing the emboli from flowing downstream.

An aspect of some embodiments of the invention includes a device with an emboli protection filter placed in the descending aorta, the device including a surface shaped and sized to expand against walls of the descending aorta, and including a cross luminal filter or filters extending across the aorta for trapping emboli and preventing the emboli from flowing downstream.

An aspect of some embodiments of the invention includes a device with a frame and/or struts designed for expanding filter material against the walls of the aortic arch and/or of the descending aorta which is suitable for deploying from a catheter and for subsequent folding back into a catheter so as to remove the device.

An aspect of some embodiments of the invention includes emboli protection filter apparatus with a cross luminal filter or filters extending across the aorta for trapping emboli and preventing the emboli from flowing downstream, the cross luminal filter(s) designed as a pocket or pockets which can be drawn shut, trapping potential emboli within the pocket (s) when removing the apparatus.

An aspect of some embodiments of the invention includes emboli protection filter apparatus with a cross luminal filter or filters extending across the descending aorta, the cross luminal filter(s) designed to allow a catheter or catheters to pass through, while continuing to act as filters around the catheter(s), enabling a trans-catheter device to pass through the filter apparatus without removing the emboli protection device.

Reference is now made to FIGS. 1A, 1B, 1C and 1D, which are intended to show an example embodiment of the invention in a general fashion, to provide an example context for some more detailed description provided below, even a description of different embodiments than depicted in FIGS. 1A, 1B, 1C and 1D. That is to say, FIGS. 1A 1B, 1C and 1D are not meant to limit the scope of the invention.

Reference is now made to FIG. 1A, which is a simplified illustration of an intra-aortic emboli protection device 100 according to an example embodiment of the invention. The emboli protection device 100 includes a porous deflector screen 102, an emboli collector 106, and a connecting portion 104.

Reference is now made to FIG. 1B, which is a simplified illustration of an intra-aortic emboli protection device 101 according to an example embodiment of the invention.

Reference is now additionally made to FIG. 1C, which is a simplified illustration of the intra-aortic emboli protection device 100 (or 101) of FIG. 1A or 1B deployed in an aorta 110 according to an example embodiment of the invention.

Reference is now additionally made to FIG. 1D, which is a simplified illustration of the intra-aortic emboli protection device 100 (or 101) of FIG. 1A or 1B as deployed in the aorta, depicting only the deployed intra-aortic emboli protection device 100 (or 101) and not the aorta, according to an example embodiment of the invention.

The porous deflector screen 102 includes a filter in order to prevent emboli from flowing into arteries 112 branching off the aortic arch 110. Potentially the emboli are diverted and flow along the descending aorta 113.

The emboli collector 106 includes a filter in order to prevent emboli deflected by porous deflector screen 102 from flowing downstream into any arteries 114 which may branch off a continuation of the descending aorta 113.

In some embodiments, such as depicted, by way of a non-limiting example, in FIG. 1B, the emboli collector 106 optionally includes one or more filter pockets 108 which optionally extend at least partway across the lumen of the descending aorta and potentially trap emboli, preventing the emboli from continuing downstream.

In some embodiments (not shown), the emboli collector 106 includes one or more filter flaps which optionally extend across the lumen of the descending aorta, either each extending separately or a plurality of the filter flaps extending across the lumen when all are extended, and potentially trap emboli, preventing the emboli from continuing downstream.

A more detailed general description now follows the above general description of one example embodiment.

An aspect of some embodiments of the invention includes a device which may be inserted into a body via a catheter, and open to a screen deflector filter shaped and designed to lie against exits from the aorta to branching arteries and filter blood to the branching arteries, and an anchor shaped and designed to anchor against walls of the aorta downstream of the filtered exits.

In some embodiments the device is maintained in a patient's body while a trans-catheter procedure is performed on the patient, the catheter and/or other devices passing upstream through the device.

In some embodiments the device is maintained in a patient's body while a procedure is performed on the patient with a tool operating upstream of the device without passing through the device, such as, by way of some non-limiting examples, in a case of heart surgery, or in a case of a trans-catheter procedure on a heart through the heart wall, and/or a trans-catheter procedure through veins.

An aspect of some embodiments of the invention includes a device which may be inserted into a body via a catheter, and open to a filter shaped and designed to push against walls of the aorta.

In some embodiment, the invention includes a device which may be inserted into a body via a catheter and open to a bi-concave elongated surface and designed to push against walls of the aorta.

In some embodiments, the filter includes a frame surrounding the entire device or portions of the device and/or struts running through or attached to the filter. The frame and/or struts potentially shape and/or press the filter against walls of the aorta.

In some embodiments, the emboli collector includes an expandable cylindrical shape which expands against walls of the descending aorta and anchors a filter which lies against exits to arteries upstream of the anchor.

In some embodiments the expandable cylindrical shape may be a stent-like shape.

In some embodiments, an emboli collector portion of the device is designed to unfurl into a cylindrical shape along walls of the descending aorta.

Optionally, a length of the emboli collector approximately corresponds to a length which is less than and possibly up to, a length of the descending aorta.

In some embodiments, a length of the emboli collector plus a length of the connecting portion approximately corresponds to a length which is less than and possibly up to, a length of the descending aorta. Optionally, a width of the emboli collector approximately corresponds to a circumference of the descending aorta, so as to completely cover the walls of the descending aorta. In some embodiments the width is greater, so as to somewhat overlap when the emboli collector is unfurled, potentially allowing for one size of a device to be used on aortas of differing circumferences, potentially requiring a smaller range of different sized devices to be used on different sized aortas.

In some embodiments, a porous deflector screen of the device is designed to unfurl into a semi-circular shape along walls of the aortic arch. In some embodiments the porous deflector screen is optionally pre-shaped to accommodate to the shape of the aortic arch.

In some embodiments, a connecting portion of the device is designed to connect the porous deflector screen and the emboli collector. The connecting portion may include a screen filter, or unfurl into a semi-circular shape along walls of the aortic arch.

In some embodiments the connecting portion is optionally pre-shaped to accommodate to the curvature of the aorta.

An aspect of some embodiments of the invention includes an emboli collector of the device with filter pockets which extend into the lumen of the unfurled device, filter downstream flow of blood and potentially trap emboli. In some embodiments, the filter pockets are at least partially attached to each other, so as to completely cover the lumen of the descending aorta.

An aspect of some embodiments of the invention includes a mechanism for re-collapsing the device into a catheter for removal.

An aspect of some embodiments of the invention includes a mechanism for closing off the filter pockets before removing the device, so as to capture and extract emboli trapped in the pockets.

An aspect of some embodiments of the invention includes a mechanism for closing off the filter pockets before removing the valve delivery system, so as to prevent potential interference with the removal of the valve delivery system.

An aspect of some embodiments of the invention includes the filter pockets being separate enough to allow a catheter to pass from a downstream side to a connecting portion side of the emboli collector portion of the device, between the pockets, enabling passage to tools aortic arch upstream while still filtering blood flowing downstream.

An aspect of some embodiments of the invention includes the emboli collector portion of the device exerting outward radial force on the walls of the descending aorta so as to potentially anchor, or at least partially anchor, the device in place.

An aspect of some embodiments of the invention includes the porous deflector screen portion of the device exerting outward radial force on the walls of the aortic so as to potentially anchor, or at least partially anchor, the device in place.

An aspect of some embodiments of the invention includes radio-opaque components attached to the device, or manufactured as part of the device, so as to potentially enable imaging the device and its location under fluoroscopy inside a patient's body.

In some embodiments, the frame, or part of the frame, is optionally radio-opaque, or radio opaque markers are attached to the frame.

In some embodiments, the struts, or part of the struts, are optionally radio-opaque, or radio opaque markers are attached to the struts.

In some embodiments, radio opaque markers are optionally attached to the filter pockets.

In some embodiments, one or more radio opaque markers are optionally attached to a wire on a downstream side of the emboli collector portion of the device, so as to enable finding the wire and capturing the device. In some embodiments, the wire includes a ring for snaring the wire. In some embodiments the wire includes a radio-opaque marker at its downstream end, to assist in imaging detecting and snaring the wire.

In some embodiments, materials used for the filter include one or more of: Nitinol, polymer such as Polyurethane, Nylon, Polyester (PET) Polypropylene (PP); a woven, knit, or knotted material of with holes; and other materials with holes which can serve as a filter.

In some embodiments, materials used for the struts include one or more of: stainless steel, Nitinol, Cr—Co.

In some embodiments, materials used for the frame include one or more of: stainless steel, Nitinol, Cr—Co.

In some embodiments, the device is constructed as one piece which includes the porous deflector screen, the connecting portion and the emboli collector as one compound construct.

In some embodiments, the device is constructed from multiple pieces. In some embodiments the pieces are interconnected by sewing, weaving, gluing, soldering, and/or any other attachment technique.

In some embodiments, the frame and/or the struts may be manufactured using laser cutting, such as used in making stent-like structures and the like, from a tube. Optionally, the device is produced from one or more strands of biocompatible wire, with further forming, braiding, pressing, heat-treating, shaping, and the like.

An aspect of some embodiments of the invention includes inserting an intra-aortic emboli protection filter apparatus according to an example embodiment of the invention, and performing a cardiac interventional procedure while the intra-aortic emboli protection filter apparatus is in place for deflecting and/or capturing potential emboli particles.

In some embodiments, the cardiac interventional procedure may be an open-heart procedure, such as, by way of a non-limiting example an on-pump procedure, where blood is made to flow by pump, and the intra-aortic emboli protection filter apparatus prevents emboli from flowing downstream through the aorta.

In some embodiments, the cardiac interventional procedure may be a trans-catheter procedure, such as, by way of a non-limiting example a TAVI/TAVR procedure, and the intra-aortic emboli protection filter apparatus prevents particles from flowing downstream through the aorta.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Before explaining at least one embodiment of the invention in detail, it is to be understood that the invention is not necessarily limited in its application to the details set forth in the following description or exemplified by the examples. The invention is capable of other embodiments or of being practiced or carried out in various ways.

Figure 2:
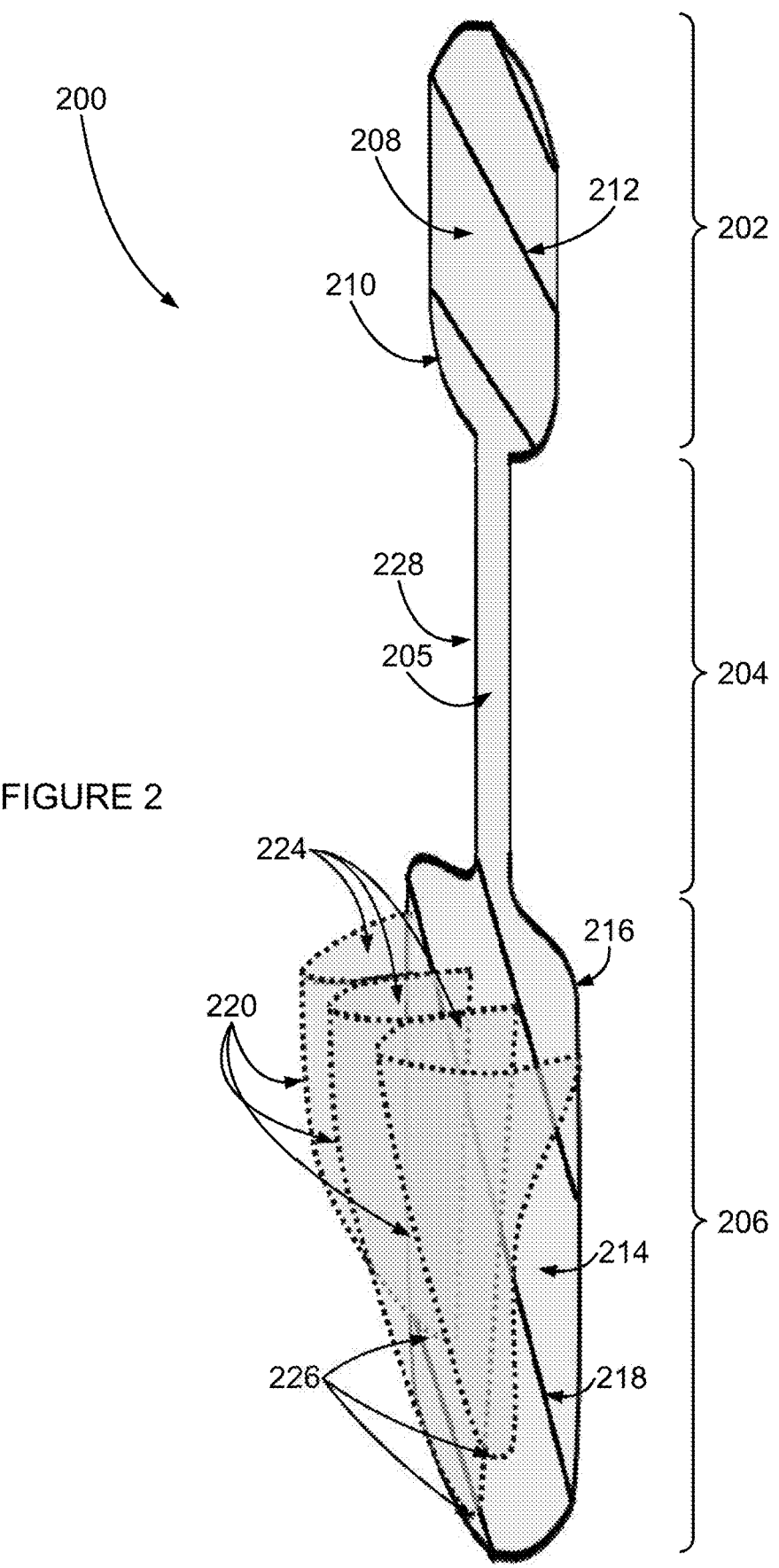
FIG. 2 is a simplified illustration of an intra-aortic emboli protection filter according to an example embodiment of the invention.

Reference is now made to FIG. 2, which is a simplified illustration of an intra-aortic emboli protection device 200 according to an example embodiment of the invention.

FIG. 2 depicts an embodiment similar to the embodiment depicted in FIG. 1B, in greater detail. FIG. 2 depicts an embodiment which has three filter pockets 220 attached to an emboli collector 206 of the emboli protection device 200.

The emboli protection device 200 includes a porous deflector screen 202, an emboli collector 206, and a connecting portion 204.

In some embodiments, the porous deflector screen 202 includes a screen filter 208, and optionally a frame 210, optionally made of a different material than the screen filter 208, which surrounds the screen filter 208.

In some embodiments, the porous deflector screen 202 optionally includes struts 212 traversing an area of the screen filter 208, which potentially shape and/or stiffen the screen filter 208.

In some embodiments, the connecting portion 204 includes a filter 205, and optionally a frame 228, optionally made of a different material than the filter 205, which surrounds the filter 205.

In some embodiments, the emboli collector 206 includes a filter 214, and optionally a frame 216, optionally made of a different material than the filter 214, which surrounds the filter 214.

In some embodiments, the emboli collector 206 optionally includes struts 218 traversing an area of the filter 214, which potentially shape and/or stiffen the filter 214.

In some embodiments, the emboli collector 206 optionally includes filter pockets 220 for filtering blood and trapping particles prevented from passing through by filter walls of the pockets 220 and the filter 214 wall of the emboli collector 206.

In some embodiments, the filter pockets 220 include an open end 224 on an upstream side of the emboli collector 206, and a closed end 226 on a downstream side of the emboli collector 206.

In some embodiments, the filter pockets 220 each have closed ends 226 at different heights, or lengths, along the emboli collector 206 of the emboli protection device 200. Having the closed ends 226 of different pockets 220 at different heights potentially provides an advantage when withdrawing the emboli protection device 200 into a catheter. If some of the filter pockets have trapped particles, the particles are potentially trapped at different lengths along the emboli collector 206 of the emboli protection device 200 potentially making less of a lump when rolled, or furled, into the catheter.

In some embodiments, the filter pockets 220 optionally have different sized open ends 224.

In some embodiments, filter the pockets 220 include a frame (not shown) along edges of the open ends 224 of the pockets 220, so as to hold the open ends 224 open. When the emboli collector 206 is in place in a descending aorta, the open ends potentially push against each other, as may be seen in FIGS. 8A and 8B, potentially blocking the lumen of the descending aorta from side to side, forcing blood to flow through a filter of the pockets.

In some embodiments, the filter pockets 220 include radio-opaque markers (not shown) along the edges of the open ends 224 of the pockets 220 so as to hold the open ends 224 open, potentially blocking the lumen of the descending aorta from side to side, forcing blood to flow through a filter of the pockets, as may be seen in FIGS. 8A and 8B.

In some embodiments the emboli protection device 200 includes a wire (not shown in FIG. 2, but shown in FIG. 1A-1D) optionally attached to the emboli collector 206.

Figure 3:
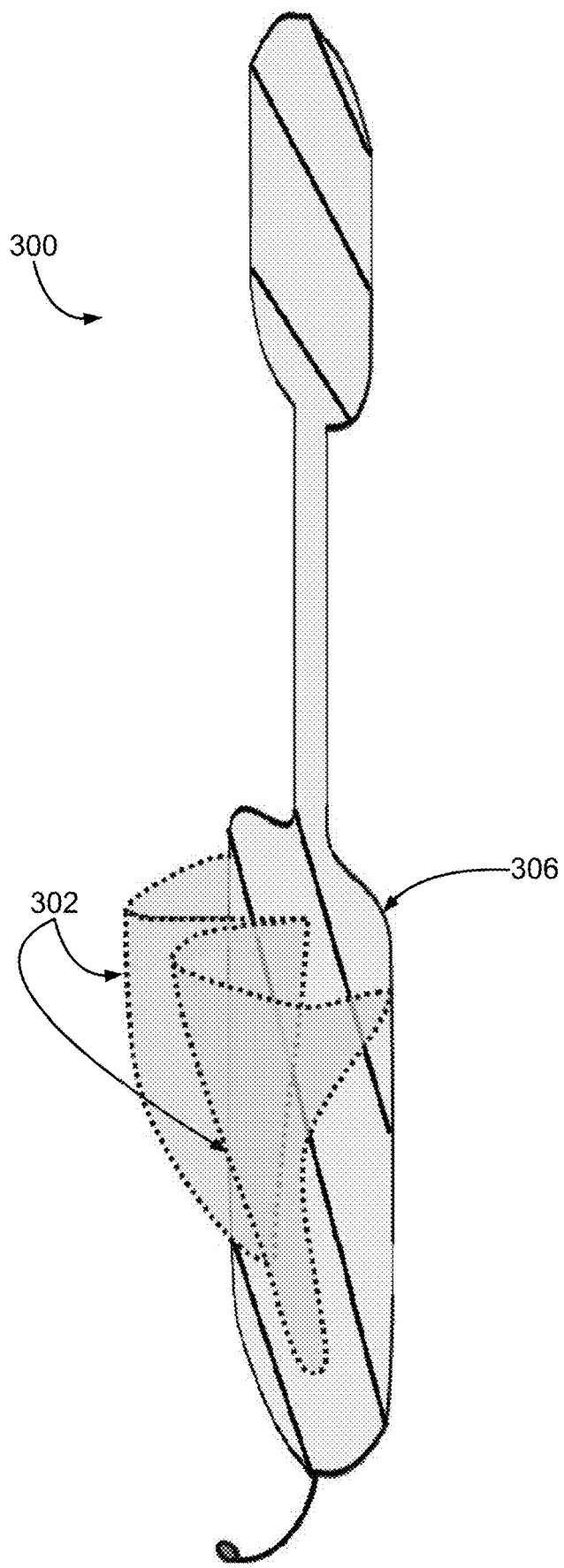
FIG. 3 is a simplified illustration of an intra-aortic emboli protection filter according to an example embodiment of the invention.

Reference is now made to FIG. 3, which is a simplified illustration of an intra-aortic emboli protection device 300 according to an example embodiment of the invention.

FIG. 3 depicts an embodiment which has two filter pockets 302 attached to an emboli collector 306 of the emboli protection device 300, while the embodiment depicted in FIG. 2 has three filter pockets 220.

Figure 4:
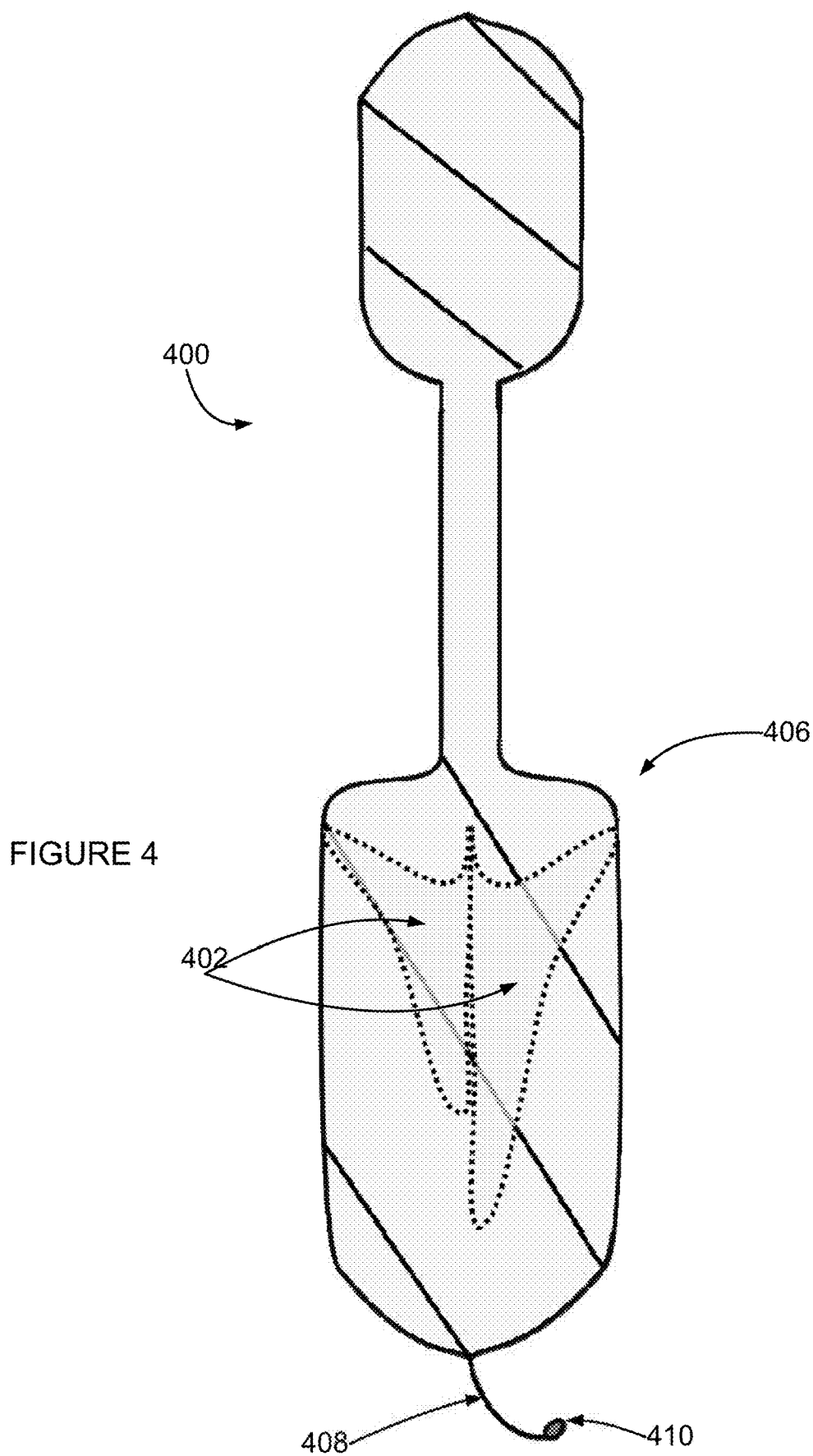
FIG. 4 is a simplified illustration of an intra-aortic emboli protection filter according to an example embodiment of the invention.

Reference is now made to FIG. 4, which is a simplified illustration of an intra-aortic emboli protection device 400 according to an example embodiment of the invention.

FIG. 4 also depicts an embodiment which has two filter pockets 402 attached to an emboli collector 406 of the emboli protection device 400.

In some embodiments the emboli protection device 400 includes a short wire 408 optionally attached to the emboli collector and in some embodiments a radio-opaque marker 410 is attached to the end of the wire 408.

In some embodiments, the radio-opaque marker 410 can be snared and a catheter can be used to remove the emboli protection device 400 from a patient's body.

In some embodiments, the radio-opaque marker 410 can serve to help a physician locate the wire 408 for removing the emboli protection device 400 from the patient's body.

Figure 5:
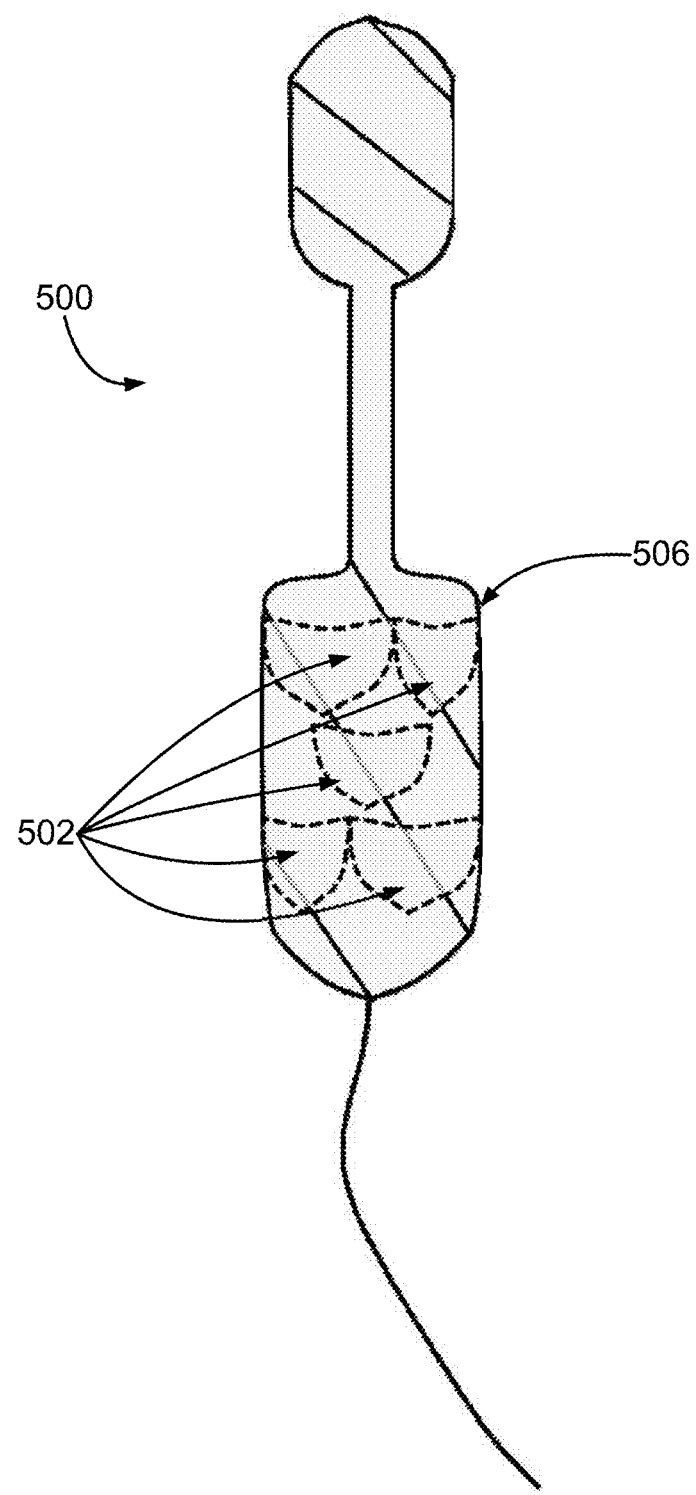
FIG. 5 is a simplified illustration of an intra-aortic emboli protection filter according to an example embodiment of the invention.

Reference is now made to FIG. 5, which is a simplified illustration of an intra-aortic emboli protection device 500 according to an example embodiment of the invention.

FIG. 5 depicts an embodiment which has five filter pockets 502 attached to an emboli collector 506 of the emboli protection device 500. The five filter pockets 502 are not all at a same height, or lengths, along the emboli collector 506 of the emboli protection device 500. Having the five pockets 502 at different heights potentially provides an advantage when withdrawing the emboli protection device 500 into a catheter. If some of the five pockets have trapped particles, the particles are potentially trapped at different lengths along the emboli collector 506 of the emboli protection device 500, potentially making less of a lump when rolled, or furled, into the catheter.

Figures 6A, 6B:
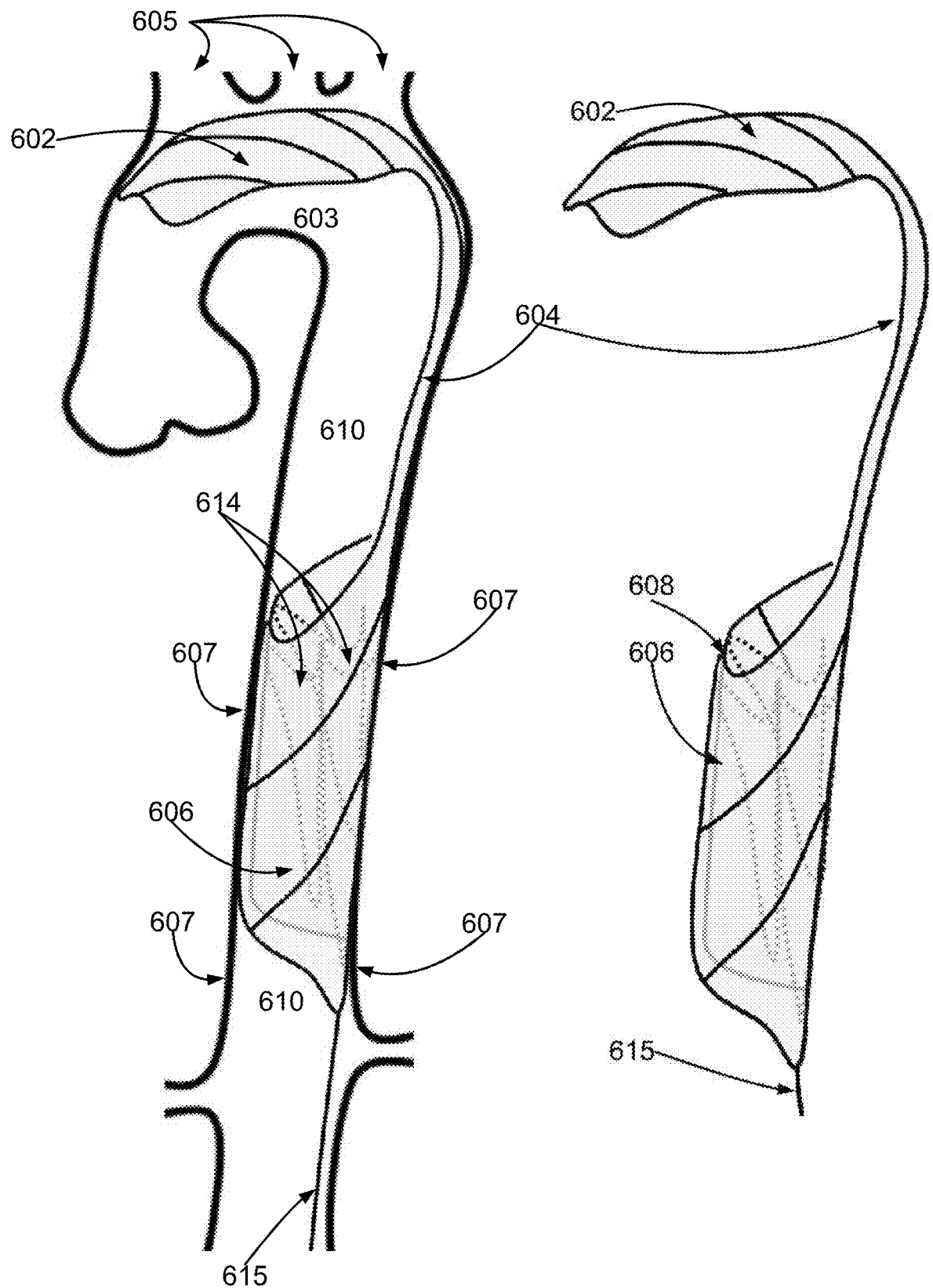
FIG. 6A is a simplified illustration of an intra-aortic emboli protection filter deployed in an aorta according to an example embodiment of the invention.
FIG. 6B is a simplified illustration of the intra-aortic emboli protection filter of FIG. 6A as deployed in the aorta, depicting only the deployed intra-aortic emboli protection filter and not the aorta.

Reference is now made to FIG. 6A, which is a simplified illustration of an intra-aortic emboli protection device deployed in an aorta according to an example embodiment of the invention.

Reference is now additionally made to FIG. 6B, which is a simplified illustration of the intra-aortic emboli protection device of FIG. 6A as deployed in the aorta, depicting only the deployed intra-aortic emboli protection device and not the aorta.

A porous deflector screen 602 of the emboli protection device is deployed in the aortic arch 603, filtering potential emboli (not shown) from potentially entering arteries 605 branching off the aortic arch 603, and diverting the potential emboli to flow along the descending aorta 610.

In some embodiments, the porous deflector screen 602 is designed to unfurl against a superior wall of the aortic arch 603 and across openings of the artery 605 which branch off the aorta, optionally creating an arch shape against walls of the aortic arch 603.

In some embodiments, the porous deflector screen 602 has an optionally partially rounded and/or planar geometry, and unfurls against the superior wall of the aortic arch. For example, porous deflector screen 602 may have the shape of a half-cylinder, a third-cylinder, or any other fraction of a cylinder (i.e. 1/n-cylinder), that has been curved inwards, towards the theoretical central axis of the cylinder. This shape is termed here a "curved cylinder portion".

For example, when made from Nitinol, porous deflector screen 602 may be shaped to a curved cylinder portion at a high temperature, cooled to a lower temperature, flattened to a planar mesh, and rolled into a cylindrical shape for insertion into an aorta with a minimally invasive surgical device.

A potential benefit of unfurling the porous deflector screen 602 to an arch shape within the aortic arch 603, with the porous deflector screen 602 pressing against artery openings 605 of the aortic arch 603, is to make a seal so that emboli potentially do not flow around the porous deflector screen 602 into the branching arteries.

In some embodiments, a connecting portion 604 is designed to push the porous deflector screen 602 against the superior wall of the aortic arch 603.

In some embodiments, connecting portion 604 connected to the porous deflector screen 602 and to an emboli collector 606 of the emboli protection device is designed to push the porous deflector screen 602 up against the superior wall of the aortic arch 603, optionally anchored by the emboli collector 606.

A potential benefit of pushing the porous deflector screen 602 against the superior wall of the aortic arch 603 is to make a seal so that emboli potentially do not flow around the porous deflector screen 602 into the branching arteries.

A potential benefit of unfurling the connecting portion 604 to a shape of a curved cylinder portion within the descending aorta 610, with the connecting portion 604 pressing against descending aorta 610 wall, is to cover the descending aorta 610 wall so that other tools used in the procedure will not scrape the descending aorta 610 wall. An emboli collector 606 of the emboli protection device is deployed in the descending aorta 610.

In some embodiments, the emboli collector 606 has an optionally rounded, or partially rounded and/or planar geometry, and unfurls against walls 607 of the descending aorta 610, optionally with edges of the emboli collector 606 somewhat overlapping, as may be seen in 608 FIG. 6B.

In some embodiments, the amount of overlap may be from 10%, 30% and even 50% of a circumference of the descending aorta 610.

In some embodiments, the emboli collector 606 of the emboli protection device includes filter pockets 614.

A potential benefit of allowing the emboli collector 606 to overlap itself is that a lumen is constructed within the walls 607 of the descending aorta 610 with the emboli collector 606 pressing against the walls 607 of the descending aorta 610 and making a seal so that emboli potentially do not flow around. Allowing different amounts of overlap enables producing such a seal with a specific width of the emboli collector 606 for any one of a wide range of descending aorta 610 circumferences.

A potential benefit of allowing the emboli collector 606 to overlap itself is that the emboli collector 606 presses against the walls 607 of the descending aorta 610, providing an anchoring effect for the emboli protection device to stay in place. Allowing different amounts of overlap enables producing such an anchor with a specific width of the emboli collector 606 for any one of a wide range of descending aorta 610 circumferences.

In some embodiments the emboli protection device includes a wire 615 optionally attached to the emboli collector 606.

In some embodiments the wire 615 assists in inserting the emboli protection device back into a catheter for removal from a patient's body.

In some embodiments the emboli protection device is intended to be inserted before a surgical procedure, and left in place for a while after the surgical procedure has ended. In some embodiments, the emboli protection device is left in the aorta after a heart surgery, and in some embodiments the emboli protection device is left in the aorta after a transcatheter surgical procedure was performed. In such cases the emboli protection device may be left in a patient's body for several minutes, hours and even days following the procedure.

Following are some details relating to the porous deflector screen of the emboli protection device.

As described above, in some embodiments the porous deflector screen is designed and shaped to lie against walls of the aorta in the aortic arch and optionally also its vicinity, block exits of arteries branching off the aorta, and filter blood flowing to the arteries.

In some embodiments, a material making up a surface of the porous deflector screen is a filter, as described herein. In some embodiments the filter of the porous deflector screen is optionally designed so as to allow sufficient blood flow to the brain. In some embodiments, the surface area of the filter of the porous deflector screen is 25-75% holes, to allow sufficient blood pressure to the brain. In some embodiments the filter is designed to have holes of a uniform or variable size in a range of 50-100, 100-150, 150-200, 200-250, or 250-300 microns, so as to potentially block emboli of a size on the order of the hole size and larger from reaching the brain.

In some embodiments, a material making up a surface of the porous deflector screen includes a low coefficient of friction coating. In some embodiments, a material making up a surface of the porous deflector screen includes an anti-thrombotic coating.

In some embodiments the porous deflector screen is produced in different sizes, to fit different sizes of aortic arch.

In some embodiments the porous deflector screen is produced in different shapes, to fit different morphologies of aortic arch.

In some embodiments the porous deflector screen is a cylindrical filter, optionally with support struts and/or wires.

A length of the porous deflector screen is optionally intended to be in a range from 3-6 cm to 12-16 cm, so as to extend along an outer circumference of the aortic arch, to fit patients having a smallest anatomy to the largest anatomy.

A width of the porous deflector screen is optionally intended to be in a range from 2 cm to 12 cm, so as to extend across exits of the arteries branching off the aorta. The width of the porous deflector screen may also be expressed in terms of covering a specific percentage of the circumference of the aorta, the percentage being in a range between 30 degrees and 270 degrees.

In some embodiments the filter material of the porous deflector screen is a same material as that of the emboli collector, potentially simplifying production of the device.

In some embodiments the porous deflector screen may include two overlapping filter surfaces. In some embodiments the porous deflector screen may include two or more different filter materials.

In some embodiments the porous deflector screen includes a frame at edges of the filter; the frame designed and shaped to form a seal between the porous deflector screen and the walls of the aorta by pressing against the walls of the aorta. In some embodiments the frame is made of a shape memory material shaped and sized to fit an aorta of a specific patient, or shaped and sized in one of several different sizes, so a physician may choose a shape and size corresponding to a shape and size of a patient' aorta, optionally based on imaging and measuring of a patient's aorta.

In some embodiments the porous deflector screen includes struts supporting the surface of the filter or mesh, optionally assisting the filter to remain against the walls of the aorta.

In some embodiments, a material making the struts is optionally a same material as making up the frame of the porous deflector screen.

In some embodiments, a material of the struts is optionally a different material than the frame of the porous deflector screen.

Following are some details relating to the connecting portion of the emboli protection device.

As described above, in some embodiments the connecting portion is designed and shaped to connect the porous deflector screen and the emboli collector, and optionally push against the porous deflector screen, helping the porous deflector screen to lie against the walls of the aorta. Another benefit of the connecting portion is to distance the emboli collector from the more tortuous part of the descending aorta to a relatively less tortuous part of the descending aorta so that the device potentially causes less interference with a procedure device, especially with a valve delivery system. Another benefit of the connecting portion is to protect the aortic wall from potentially harmful interaction by the valve delivery system.

In some embodiments, the connecting portion includes a frame. In some embodiments, the connecting portion optionally includes a filter. In some embodiments, the filter has identical or similar characteristics to the filter of the porous deflector screen. In some embodiments, the connecting portion is a filter screen with support struts and/or wires. In some embodiments, the connecting portion is a filter cylinder with support struts and/or wires. In some embodiments, the material making the connecting portion optionally does not include a filter. In some embodiments, a material making up a surface of the connecting portion is not a filter, but rather a sealed material. In some embodiments, a material making up a surface of the connecting portion includes a coating of a low coefficient of friction. In some embodiments, a material making up a surface of the connecting portion includes an anti-thrombotic coating.

In some embodiments the connecting portion is produced in different sizes, to fit different sizes and shapes of descending aorta.

In some embodiments a length of the connecting portion is optionally in a range from 2 cm to 20 cm, so as to extend from a downstream side of the porous deflector screen to the upstream part of the emboli collector.

A width of the connecting portion is optionally intended to be in a range from 5 mm to 6 cm, so as to provide sufficient strength to push against the porous deflector screen and against the emboli collector.

A width of the connecting portion is optionally intended to be in a range from 5 degrees to 180 degrees of a circumference of the aorta.

In some embodiments, a material making the connecting portion is optionally a same material as making up the frame and/or the struts of the porous deflector screen, potentially simplifying production of the device.

In some embodiments, a material making the connecting portion is optionally a different material as making up the frame and/or of the porous deflector screen.

In some embodiments the connecting portion is shaped and sized to fit an aorta of a specific patient, or shaped and sized in one of several different sizes, so a physician may choose a shape and size corresponding to a shape and size of a patient' aorta, optionally based on imaging and measuring of a patient's aorta.

Following are some details relating to the emboli collector of the emboli protection device.

As described above, in some embodiments the emboli collector is designed and shaped to lie against walls of the aorta in the descending aorta and optionally also its vicinity, anchoring the device; optionally filtering blood flowing downstream; and optionally including a filter for filtering blood flowing downstream while still enabling passage of catheters upstream through the filter.

In some embodiments, a material making up a surface of the emboli collector is a filter, as described herein, designed to filter blood flowing into branching arteries covered by the emboli collector.

In some embodiments, a material making up a surface of the emboli collector includes a coating of a low coefficient of friction. In some embodiments, a material making up a surface of the emboli collector includes an anti-thrombotic coating.

In some embodiments, such a filter has identical or similar characteristics to the filter of the porous deflector screen. Alternatively, it may have holes of a larger size, such as 300-350, 350-400, 400-450, 450-500 microns or larger. In some embodiments such a filter includes a same material as the porous deflector screen, potentially simplifying production of the emboli protection device.

In some embodiments, a material making up a surface of the emboli collector is not a filter, but rather a sealed material.

In some embodiments, a material making up a cross luminal filter and/or pocket of the emboli collector is a filter, or a mesh, as described herein, designed to filter blood flowing downstream of the emboli collector of the emboli protection device.

Again, as detailed above, the material making up the cross luminal filter and/or pocket of the emboli collector may have identical or similar characteristics to the filter of the porous deflector screen. Alternatively, it may have holes of a smaller size, such as 10-30 or 30-50 microns or smaller.

In some embodiments, a material making up the filter includes a coating of a low coefficient of friction. In some embodiments, a material making up the filter includes an anti-thrombotic coating.

In some embodiments the emboli collector is produced in different sizes, to fit different sizes of aortas.

In some embodiments the cross luminal filter and/or pocket of the emboli collector is produced in different sizes, to fit different sizes of aortas.

A length of the emboli collector is optionally intended to be in a range from 2 cm to 20 cm.

In some embodiments the emboli collector is shaped as planner/screen that unfurls to a cylinder shape. A width of the emboli collector is optionally intended to be in a range from 6 cm to 12 cm, so as to extend along most of an entire circumference of the aorta, and, in some embodiments, to extend more than an entire circumference of the aorta and overlap itself. The width of the emboli collector may also be expressed in terms of covering a specific percentage of the circumference of the aorta, the percentage being in a range between 100% and 150%.

A potential benefit of the overlap is that a specific width may be used for a range of patient sizes, for a range of circumferences of the aorta, and overlap by different amounts, without losing an overlap effect.

A potential benefit of the overlap is that the emboli collector produces a seal against the aortic wall and/or between the pockets. In some embodiments the emboli collector includes a frame at edges of the filter or mesh; the frame designed and shaped to press against walls of the aorta, potentially anchoring the emboli collector against walls of the aorta.

In some embodiments the emboli collector includes a frame at edges of the filter or mesh, the frame designed and shaped to form a seal between the emboli collector and the walls of the aorta by pressing against the walls of the aorta, potentially preventing blood and/or emboli from flowing between the emboli collector and walls of the aorta. In some embodiments the frame is made of a shape memory material shaped and sized to fit an aorta of a specific patient, or shaped and sized in one of several different sizes, so a physician may choose a shape and size corresponding to a shape and size of a patient' aorta, optionally based on imaging and measuring of a patient's aorta.

In some embodiments the emboli collector is shaped and sized as a single, cylindrical shaped frame with a diameter ranging from 1 cm to 6 cm.

In some embodiments the emboli collector is a stent-like cylinder frame.

A potential benefit of the oversize is to create a radial force on the aorta wall as an anchoring mechanism.

In some embodiments the emboli collector includes struts supporting the surface of the emboli collector, optionally assisting the emboli collector to anchor against the walls of the aorta.

In some embodiments, a material making the struts is optionally a same material as making up the frame of the porous deflector screen.

Figures 6C, 6D:
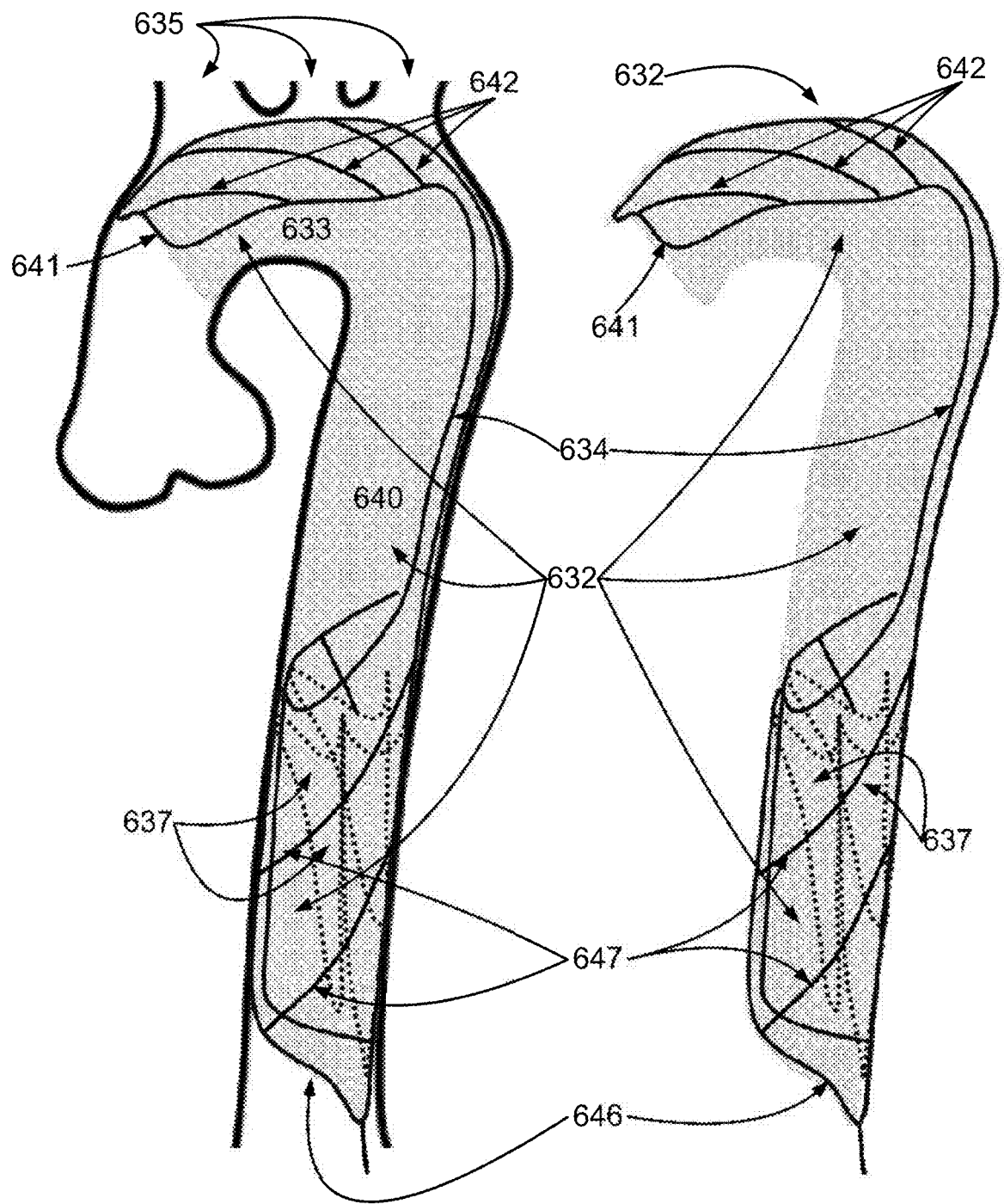
FIG. 6C is a simplified illustration of an intra-aortic emboli protection filter deployed in an aorta according to an example embodiment of the invention.
FIG. 6D is a simplified illustration of the intra-aortic emboli protection filter of FIG. 6C as deployed in the aorta, depicting only the deployed intra-aortic emboli protection filter and not the aorta.

Reference is now made to FIG. 6C, which is a simplified illustration of an intra-aortic emboli protection device deployed in an aorta according to an example embodiment of the invention.

Reference is now additionally made to FIG. 6D, which is a simplified illustration of the intra-aortic emboli protection device of FIG. 6C as deployed in the aorta, depicting only the deployed intra-aortic emboli protection device and not the aorta.

A cylindrical filter 632 extending along a length of the emboli protection device is optionally deployed in the aortic arch 633, and in the descending aorta 640, filtering potential emboli (not shown) from potentially entering arteries 635 branching off the aortic arch 633, and diverting the potential emboli to flow along the descending aorta 640.

In some embodiments the cylindrical filter 632 extends 60% to 110% of a length of a frame 641 and/or struts 642.

A frame 641 and/or struts 642 of a porous deflector screen of the emboli protection device are designed to unfurl against the superior wall of the aortic arch 633 and across openings of the arteries 635 which branch off the aorta, optionally creating an arch shape against walls of the aortic arch 633, and pushing the cylindrical filter 632 against the walls of the aortic arch 633.

In some embodiments, a connecting portion 634 is designed to push the frame 641 and/or struts 642 of the porous deflector screen of the emboli protection device 632 against the superior wall of the aortic arch 633.

In some embodiment the connecting portion 634 is designed to protect the aorta wall from a potentially harmful interaction with the valve delivery system.

In some embodiments, the connecting portion 634 connected to the frame 641 and/or struts 642 of the porous deflector screen of the emboli protection device and to a frame 646 and/or struts 647 of an emboli collector of the emboli protection device is designed to push the frame 641 and/or struts 642 of the porous deflector screen up against the superior wall of the aortic arch 633, optionally anchored by the frame 646 and/or struts 647 of the emboli collector.

In some embodiments the emboli protection device includes filter pockets 637 in an emboli collector of the emboli protection device, similar to the filter pockets 614 of FIGS. 6A and 6B.

Following are some details relating to the optional struts and optional frame.

Figure 6E:
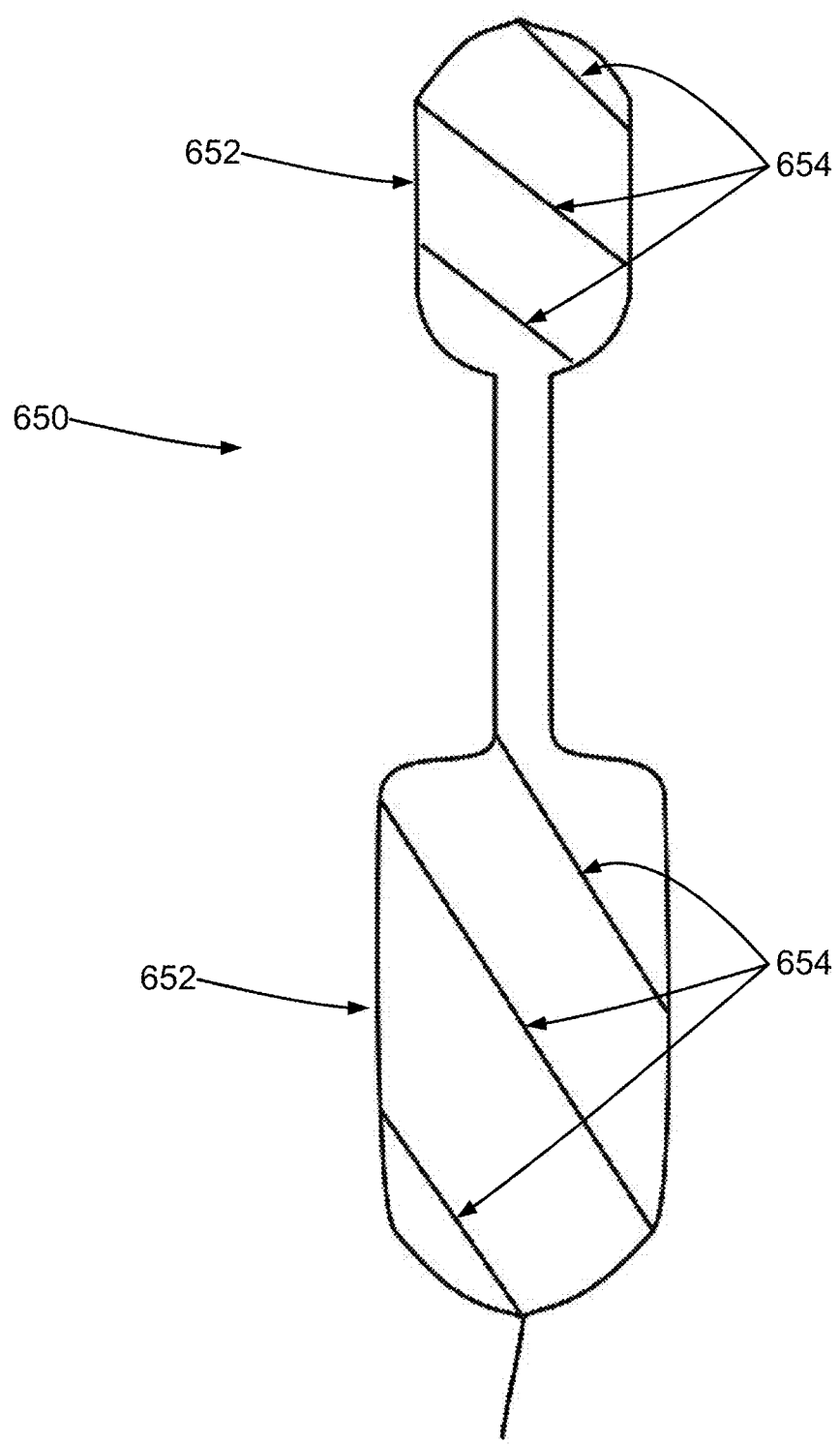
FIG. 6E is a simplified illustration of an intra-aortic emboli protection filter according to an example embodiment of the invention.

Reference is now made to FIG. 6E, which is a simplified illustration of an intra-aortic emboli protection device 650 according to an example embodiment of the invention.

FIG. 6E depicts the emboli protection device 650 without a planar filter, showing only an optional frame 652 and optional struts 654.

FIG. 6E depicts an example embodiment design of the frame 652 and the struts 654 which are suitable for folding into a catheter, for delivery into a patient's body.

The frame 652 optionally extends around a perimeter of the emboli protection device 650, and optionally expands the emboli protection device 650 to its intended shape when deployed from inside a catheter (not shown). In some embodiments the frame is made of a shape memory material.

In some embodiments the struts 654 optionally assist the frame 652 in expanding a filter (not shown).

In some embodiments the struts 654 are optionally attached to the frame diagonally with reference to a long axis of the emboli protection device 650. In some embodiments an angle of the struts relative to the long axis of the emboli protection device 650 is in a range between 60° and 5°. In some embodiments an angle of the struts relative to the long axis of the emboli protection device 650 is less than 45°, and even less than 30°.

In such embodiments the struts 654 potentially allow easier collapsing of the emboli protection device 650 into a catheter. In some embodiments the struts are made of a shape memory material.

Figure 7A:
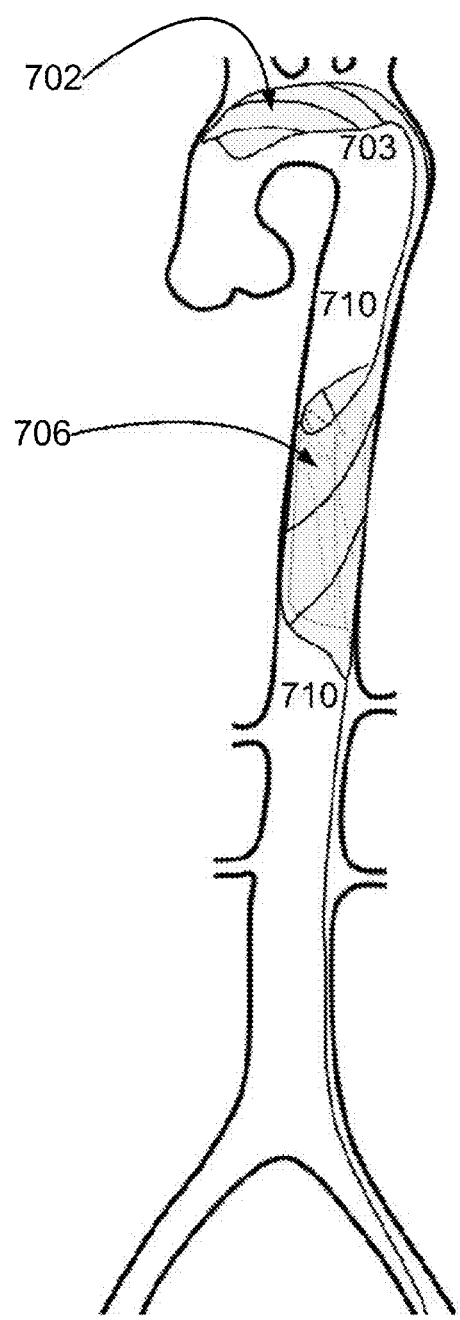
FIG. 7A is a simplified illustration of an intra-aortic emboli protection filter deployed in an aorta according to an example embodiment of the invention.

Reference is now made to FIG. 7A, which is a simplified illustration of an intra-aortic emboli protection device deployed in an aorta according to an example embodiment of the invention.

FIG. 7A depicts the intra-aortic emboli protection filter deployed in the aorta, ready for an optional process of inserting one or more pigtail catheters, wires, valvuloplasty balloon and/or TAVI/TAVR valve delivery systems through the emboli protection device.

A porous deflector screen 702 of the emboli protection filter is deployed in the aortic arch 703, filtering potential emboli (not shown) from potentially entering arteries branching off the aortic arch 703, and diverting the potential emboli to flow along the descending aorta 710.

An emboli collector 706 of the emboli protection filter is deployed in the descending aorta 710.

Figure 7B:
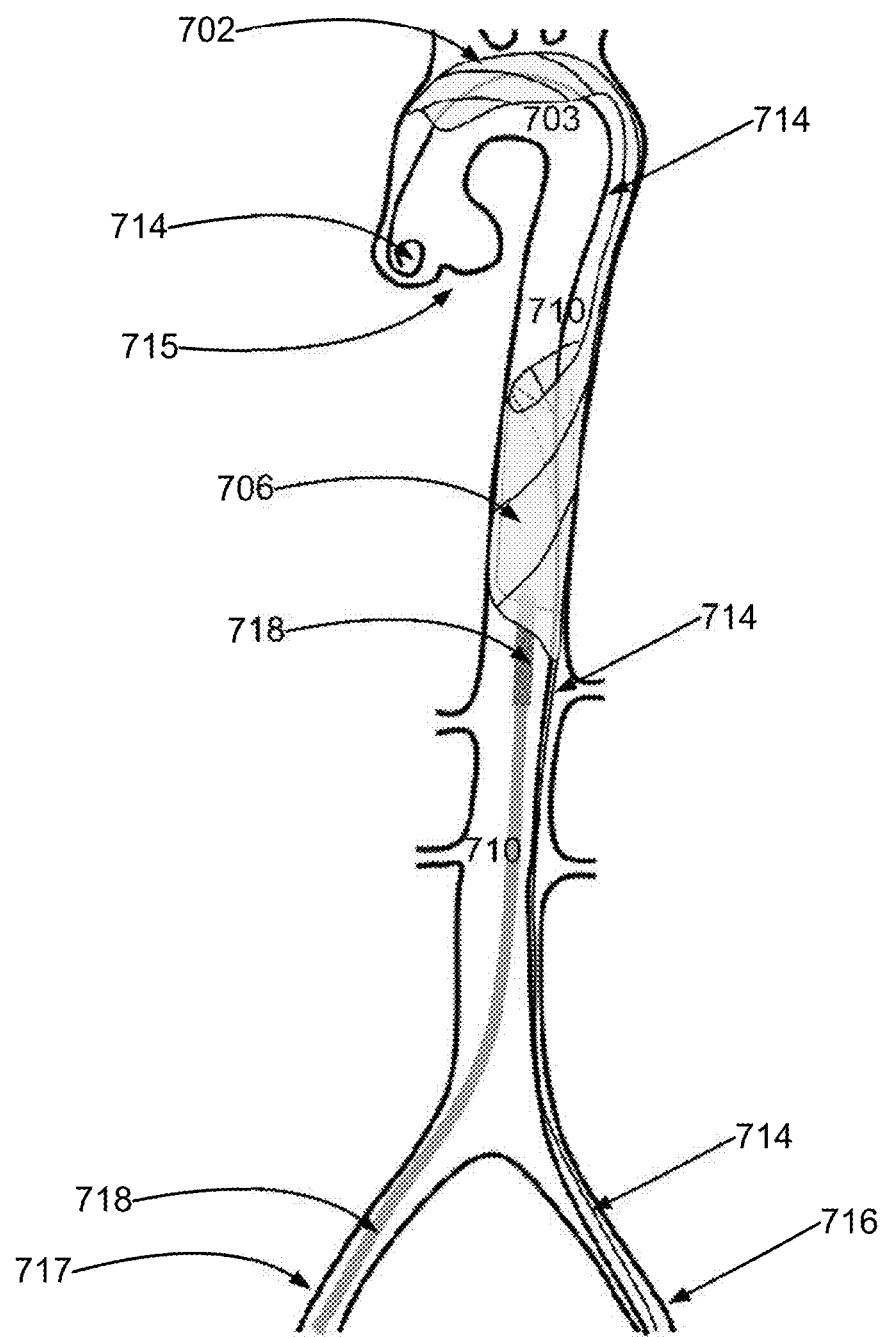
FIG. 7B is a simplified illustration of the intra-aortic emboli protection filter of FIG. 7A deployed in the aorta according to an example embodiment of the invention.

Reference is now made to FIG. 7B, which is a simplified illustration of the intra-aortic emboli protection filter of FIG. 7A deployed in the aorta according to an example embodiment of the invention.

FIG. 7B depicts inserting a TAVI/TAVR valve delivery system through the emboli protection filter, as part of a trans-catheter cardiac intervention, by way of a non-limiting example, TAVI/TAVR, performed in conjunction with an intra-aortic emboli protection filter deployed in an aorta.

A porous deflector screen 702 of the emboli protection filter is deployed in the aortic arch 703, filtering potential emboli (not shown) from potentially entering arteries branching off the aortic arch 703, and diverting the potential emboli to flow along the descending aorta 710.

An emboli collector 706 of the emboli protection filter is deployed in the descending aorta 710.

A pigtail catheter 714 is depicted as having been introduced through a femoral artery 716, through the descending aorta 710, through the aortic arch 703, and to the aortic valve 715.

A valve delivery system 718 is shown as having been introduced through a second femoral artery 717, through the descending aorta 710, and up to the emboli collector 706 of the emboli protection filter.

Figure 7C:
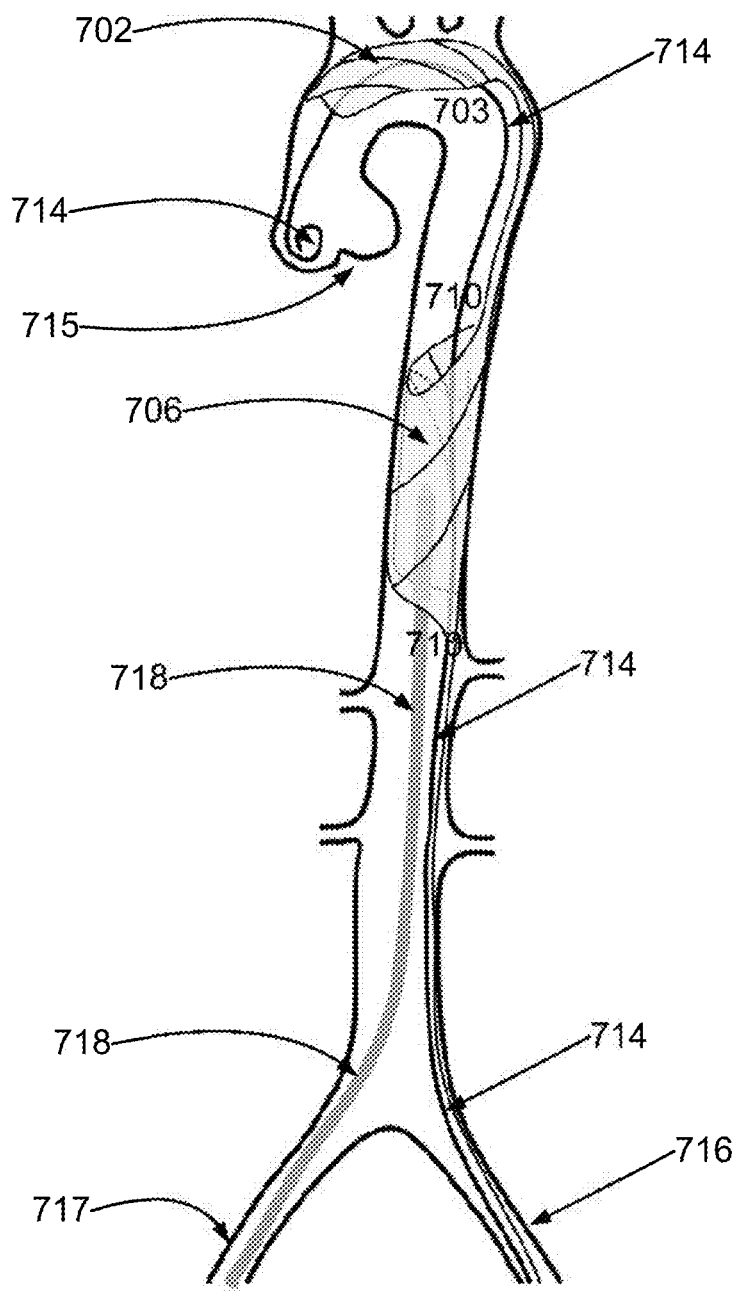
FIG. 7C is a simplified illustration of the intra-aortic emboli protection filter of FIG. 7A deployed in the aorta according to an example embodiment of the invention.

Reference is now made to FIG. 7C, which is a simplified illustration of the intra-aortic emboli protection filter of FIG. 7A deployed in the aorta according to an example embodiment of the invention.

FIG. 7C depicts a continuation of the process started in FIG. 7B.

The porous deflector screen 702 of the emboli protection filter is deployed in the aortic arch 703, as in FIG. 7A.

The emboli collector 706 of the emboli protection filter is deployed in the descending aorta 710, as depicted in FIG. 7A.

The pigtail 714 is depicted as having reached the aortic valve 715, as in FIG. 7B.

The catheter 718 is shown as having passed through the second femoral artery 717, through the descending aorta 710, and is beginning to pass through the emboli collector 706 of the emboli protection filter, between the filter pockets (not shown in FIG. 7C, but shown in FIGS. 1A, 2, 3, 4, 5, and 6A).

In some embodiments, a force required to push a catheter between the filter pockets is in a range between 1 gram and 5 kilograms.

Figure 7D:
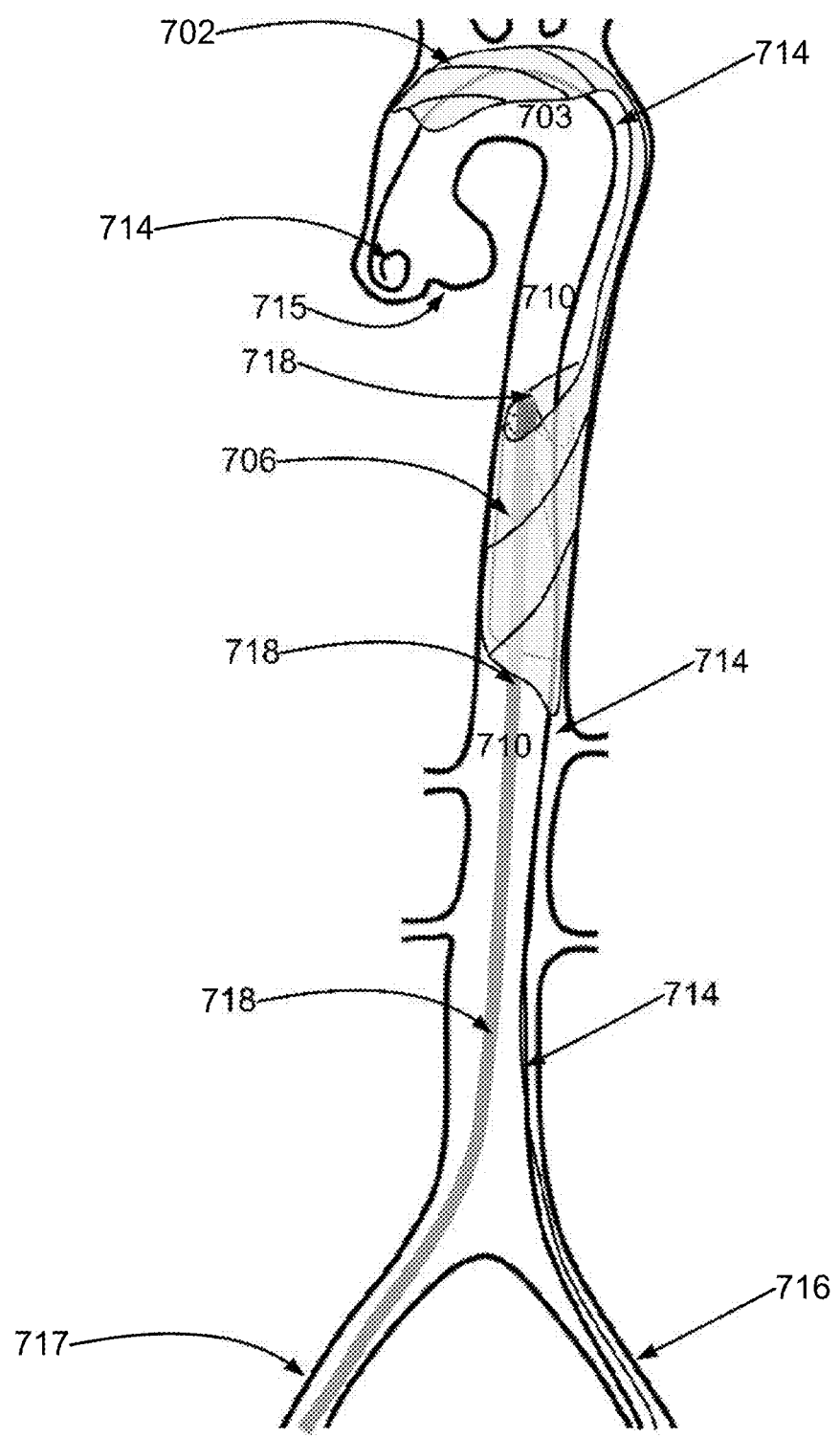
FIG. 7D, which is a simplified illustration of the intra-aortic emboli protection filter of FIG. 7A deployed in the aorta according to an example embodiment of the invention.

Reference is now made to FIG. 7D, which is a simplified illustration of the intra-aortic emboli protection filter of FIG. 7A deployed in the aorta according to an example embodiment of the invention.

FIG. 7D depicts a continuation of the process of the trans-catheter cardiac surgical intervention started in FIG. 7B.

The porous deflector screen 702 of the emboli protection filter is deployed in the aortic arch 703, as in FIG. 7A.

The emboli collector 706 of the emboli protection filter is deployed in the descending aorta 710, as depicted in FIG. 7A.

The pigtail 714 is depicted as having reached the aortic valve 715, as in FIG. 7B.

The catheter 718 is shown as having passed through the second femoral artery 717, through the descending aorta 710, and through the emboli collector 706 of the emboli protection filter, between the filter pockets (not shown in FIG. 7D, but shown in FIGS. 1A, 2, 3, 4, 5, and 6A).

Figure 7E:
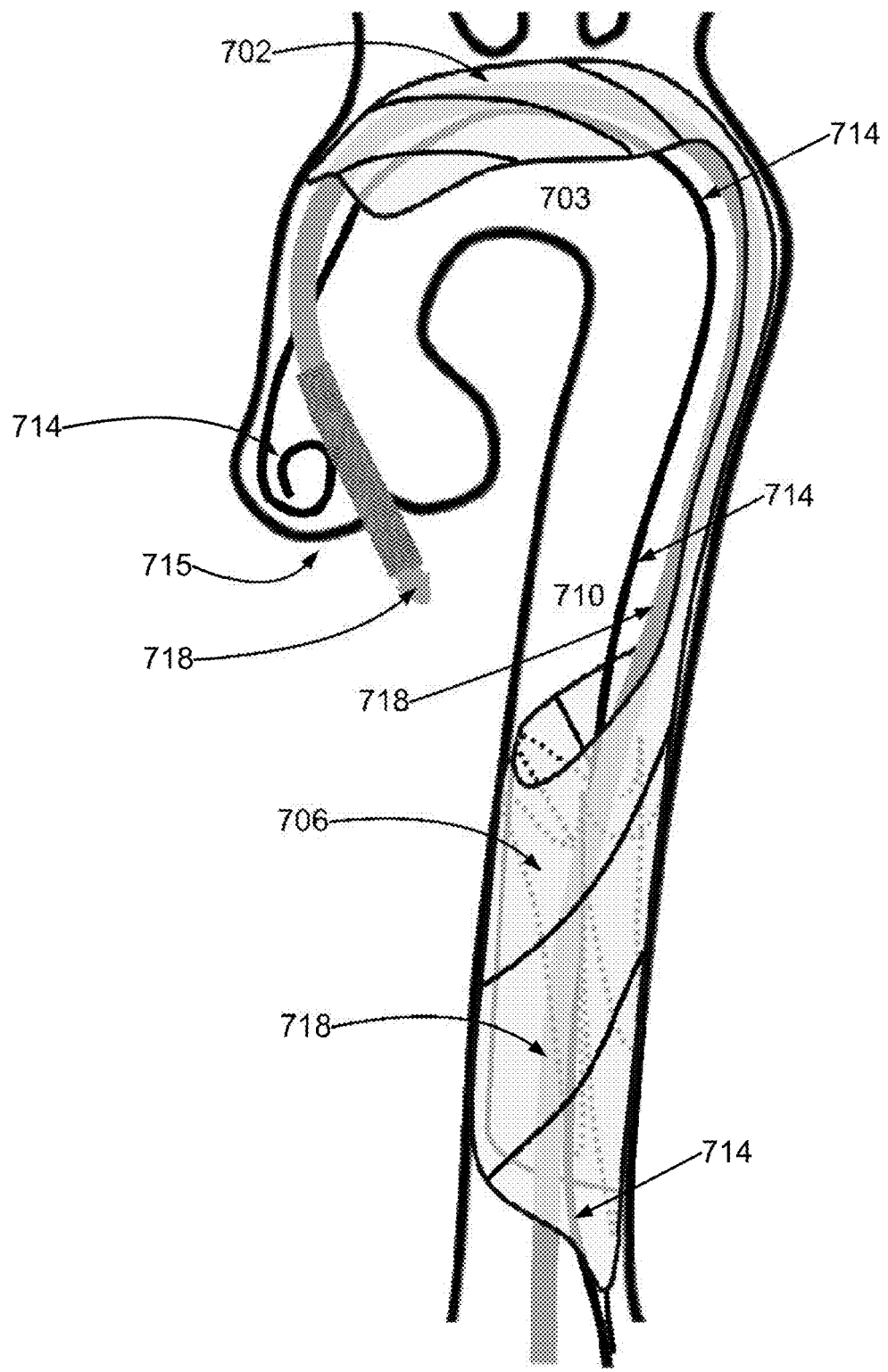
FIG. 7E, which is a simplified illustration of the intra-aortic emboli protection filter of FIG. 7A deployed in the aorta according to an example embodiment of the invention.

Reference is now made to FIG. 7E, which is a simplified illustration of the intra-aortic emboli protection filter of FIG. 7A deployed in the aorta according to an example embodiment of the invention.

FIG. 7E depicts a continuation of the process of the trans-catheter cardiac surgical intervention started in FIG. 7B.

The porous deflector screen 702 of the emboli protection filter is deployed in the aortic arch 703, as in FIG. 7A.

The emboli collector 706 of the emboli protection filter is deployed in the descending aorta 710, as depicted in FIG. 7A.

The pigtail 714 is depicted as having reached the aortic valve 715, as in FIG. 7B.

The catheter 718 is shown as having passed through the second artery 717, through the descending aorta 710, and through the emboli collector 706 of the emboli protection filter, between the pockets, through the aortic arch 703, to the aortic valve 715, and through the aortic valve 715.

Reference is now made to FIG. 8A, which is a simplified cross-sectional illustration of an emboli collector of an intra-aortic emboli protection filter as deployed in an aorta according to an example embodiment of the invention.

FIG. 8A depicts a cross-section of a surface 802 of the emboli collector, including cross-sections of three filter pockets 804. Walls 806 of the pockets are adjacent to each other, making blood flow through filter sides of the pockets 804. In some embodiments, the walls 806 of the pockets are partially attached to each other.

In some embodiments the walls 806 of the filter pockets coapt, forcing downstream flow of blood to flow through the filter pockets 804.

A section of overlap 808 of the filter of the emboli collector is also depicted. In the section of overlap, it is also shown that the walls of the filter pockets 806 may also fold and overlap.

In some embodiments the emboli collector includes a frame, struts, or even the filter itself, which is/are elastic or a shape-memory material, and the emboli collector seeks to expand, pushing against walls of the descending aorta (not shown in FIG. 8A). The pushing against walls of the descending aorta potentially produces a good seal between the emboli collector and the walls of the descending aorta, preventing blood and/or at least emboli from flowing around the filter instead of through the filter.

In some embodiments, the filter pockets of the emboli collector includes a frame around an opening of the pockets, or, struts, or the filter of the pockets may include are elastic or a shape memory material, inducing walls of the pockets to push against each other, take up all or most of the cross section of a lumen of the descending aorta so that all or most blood be filtered through a filter, and potentially also keep the open end of the pockets open to blood flow.

In some embodiments the filter pockets of the emboli collector includes radio-opaque markers attached to edges of openings of the pockets.

In some embodiments the radio-opaque markers attached to edges of the opening of the pockets, are used to potentially assist imaging systems in showing that the emboli collector is in its correct place and/or that the edges have properly closed the lumen of the descending aorta.

Reference is now made to FIG. 8B, which is a simplified cross-sectional illustration of an emboli collector of an intra-aortic emboli protection filter as deployed in an aorta similar to the drawing in FIG. 8A.

FIG. 8B depicts a cross-section of a pigtail catheter 812 and a cross-section of a valve delivery system 814 which have been pushed through the emboli collector of the intra-aortic emboli protection filter, between pockets 804 of the emboli collector of the intra-aortic emboli protection filter.

FIG. 8B depicts a cross-section of a surface 802 of the emboli collector, including cross-sections of three filter pockets 804, similar to the depiction in FIG. 8A. Walls 806 of the pockets are adjacent to each other, making blood flow through filter sides of the pockets 804, similar to the depiction in FIG. 8A.

A section of overlap 808 of the filter of the emboli collector is also depicted. In the section of overlap, it is also shown that the walls of the filter pockets 806 may also fold and overlap, similar to the depiction in FIG. 8A.

Reference is now made to FIG. 9A, which is a simplified flow chart illustration of a method for protecting a patient against flow of emboli from an aorta to branching arteries according to an example embodiment of the invention.

The method of FIG. 9A includes:

providing a device with a porous deflector screen comprising a filter, arranged to expand and to cover entrances to arteries branching from an aorta; an emboli collector comprising an expandable shape arranged to expand and to lie along walls of a descending aorta, pushing against walls of the descending aorta for anchoring the porous deflector screen; and a connecting portion for connecting the porous deflector screen and the emboli collector (912); and inserting the device via a catheter into an aorta, such that the porous deflector screen is placed in the aortic arch, the filter of the porous deflector screen blocking exits to arteries branching off the aortic arch; and the emboli collector is placed at the descending aorta and unfurled to lie along walls of the descending aorta (914).

In some embodiments, the operation on the heart of the patient is an on-pump cardiac surgery on the heart of the patient.

In some embodiments, the device is left within the aorta after conclusion of the on-pump cardiac surgery, for a period of minutes, hours and even days.

In some embodiments, the device is left within the aorta after conclusion of the on-pump cardiac surgery, for a period of 1 to 60 minutes, 1 to 24 hours and even 1 to several days.

In some embodiments, the device is left within the aorta after conclusion of the on-pump cardiac surgery, even after patient is allowed to leave his bed and move around.

In some embodiments, the device is left within the aorta after conclusion of the on-pump cardiac surgery, and the patient is given anti-clotting medicine.

In some embodiments, a catheter is used to remove the device from the aorta.

Reference is now made to FIG. 9B, which is a simplified flow chart illustration of a method for protecting a patient against flow of emboli from an aorta to branching arteries according to an example embodiment of the invention.

The method of FIG. 9B includes:

providing a device with a porous deflector screen comprising a flexible, optionally rounded or partially rounded, planar filter, arranged for placing in an aortic arch; an emboli collector including a flexible, optionally cylinder, rounded or partially rounded, planar filter arranged to unfurl from a catheter and extend to lie along walls of the descending aorta, covering an entire circumference of the descending aorta and edges of the filter partially overlapping and a filter pocket attached to arranged to extend from the walls of the descending aorta into a center of a lumen of the descending aorta, for trapping emboli flowing downstream; and a connecting portion for connecting the proximal portion and the emboli collector (902);

and inserting the device via a catheter into an aorta, such that the porous deflector screen is placed at the aortic arch, the flexible planar filter blocking exits to arteries branching off the aortic arch; and the emboli collector is placed at the descending aorta and unfurled to lie along walls of the descending aorta (904).

In some embodiments, an opening of the filter pocket is closed prior to removing the device from the aorta.

In some embodiments, an opening of the filter pocket is closed by pulling a cord for drawing closed the mouth of the filter pocket prior to removing the device from the aorta.

In some embodiments, a procedure is performed on a heart of the patient by passing a catheter through the emboli collector of the device, next to the pocket.

In some embodiments, the above-mentioned pocket includes two or more pockets, and the performing a procedure on a heart of the patient includes passing a catheter through the emboli collector of the device, between the plurality of pockets.

In some embodiments, the procedure on the heart of the patient is an on-pump cardiac surgery on the heart of the patient.

In some embodiments, the device is left within the aorta after conclusion of the on-pump cardiac surgery, for a period of minutes, hours and even days.

In some embodiments, a catheter is used to remove the device from the aorta.

In some embodiments material making up the filter is flexible, and a shaping of the various portions of the device is performed by a frame and/or struts attached to the filter.

In some embodiments, the material making up the filter is not flexible, and a shaping of the various portions of the device is performed by a frame and/or struts attached to the filter.

In some embodiments, the material making up the filter is a shape-memory material, and the filter itself unfurls to expand and take up its intended shape in the aorta.

In some embodiments filter pore size is approximately in a range from 50 microns to 500 microns.

In some embodiments the material making up the frame and/or struts is a shape-memory material, such as Nitinol.

In some embodiments the material making up the frame and/or struts is a stainless steel material.

In some embodiments the material making up the frame and/or struts is a Cr—Co material.

In some embodiments a mechanism is included which enables a physician to close open ends of the filter pockets, so that particles trapped in the filter pockets remain in the pockets and are not let loose in a process of removing the intra-aortic emboli protection filter from a patient's body.

In some embodiments a mechanism is included which enables a physician to close open ends of the filter pockets, so that the valve delivery system can be removed with potentially less interference from the pockets.

Figure 10:
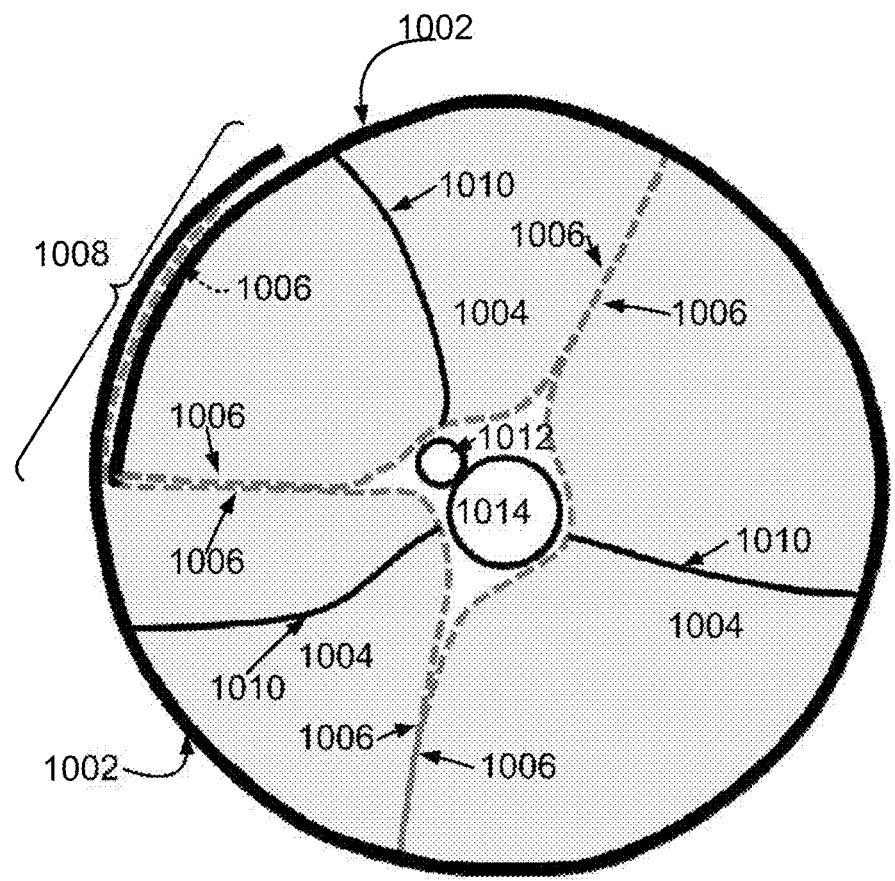
FIG. 10 is a simplified cross-sectional illustration of an emboli collector of an intra-aortic emboli protection filter as deployed in an aorta according to an example embodiment of the invention.
Figure 11A:
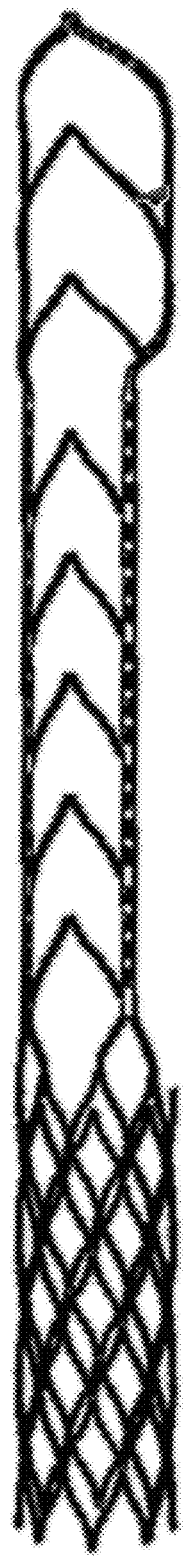
FIGS. 11A-11D are schematic illustrations of alternative frame structures for an embolic protection device according to example embodiments of the invention.
Figure 11B:
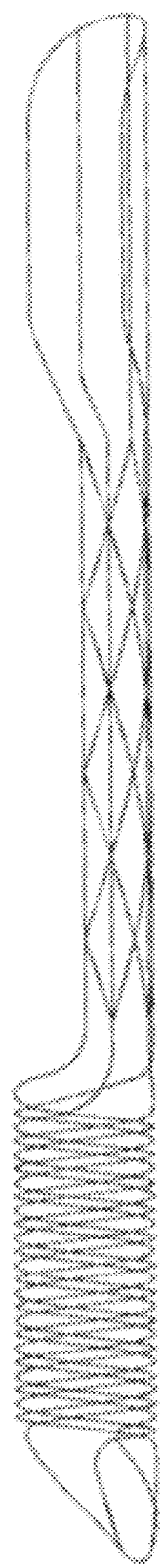
Figure 11C:
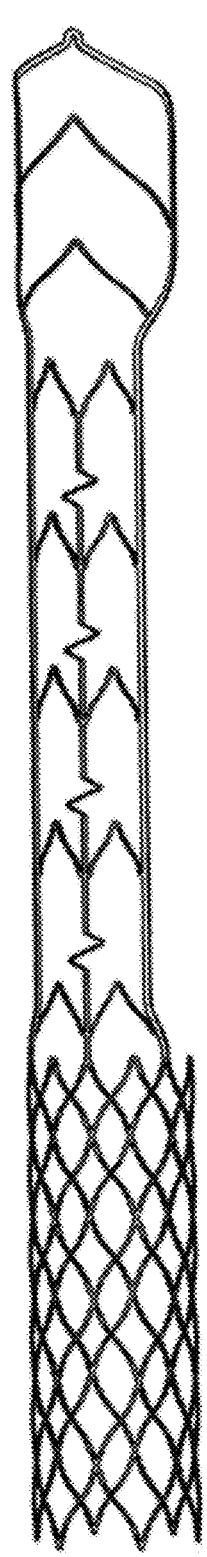
Figure 11D:
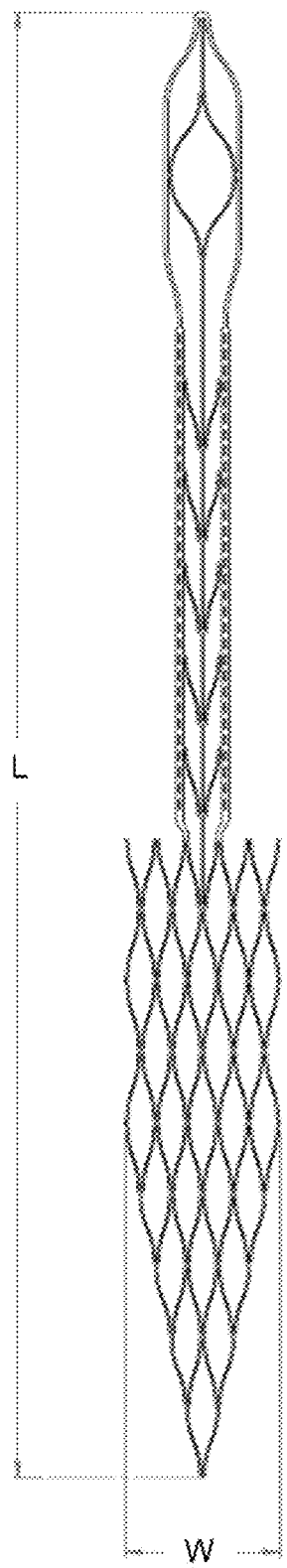

Reference is now made to FIG. 10, which is a simplified cross-sectional illustration of an emboli collector of an intra-aortic emboli protection filter as deployed in an aorta according to an example embodiment of the invention.

FIG. 10 is intended to depict a simple mechanism for closing open ends of filter pockets in the emboli collector of an intra-aortic emboli protection filter.

FIG. 10 depicts a cross-section of a surface 1002 of the emboli collector, including cross-sections of three filter pockets 1004, similar to the depiction in FIG. 8A. Walls 1006 of the pockets are adjacent and/or partially attached to each other, making blood flow through filter sides of the pockets 1004, similar to the depiction in FIG. 8A.

A section of overlap 1008 of the filter of the emboli collector is also depicted. In the section of overlap, it is also shown that the walls of the filter pockets 1006 may also fold and overlap, similar to the depiction in FIG. 8A.

FIG. 10 also depicts a cross-section of a pigtail catheter 1012 and a cross-section of a valve delivery system 1014 which have been pushed through the emboli collector of the intra-aortic emboli protection filter, between pockets 1004 of the emboli collector of the intra-aortic emboli protection filter, similar to FIG. 8B.

FIG. 10 also depicts optional wires 1010 or strings attached to walls 1006 or edges of the pockets 1004, which can be pulled to close the open pockets 1004.

In some embodiments (not shown) the optional wires 1010 or strings are optionally threaded through edges of the pockets, enabling to draw the pockets shut like a purse-string.

In some embodiments the mechanism for closing open ends of the filter pockets includes a drawstring through edges of the pockets, which can be pulled by a physician, to close the open ends of the pockets.

In some embodiments radio-opaque markers are used in one or more of: the porous deflector screen of the device; the connecting portion of the device; the emboli collector of the device; the open end or edge of the filter pockets of the emboli collector of the device; and the end of the wire attached to the emboli collector of the device.

In some embodiments radio-opaque markers are used in a drawstring used to close an open end of the filter pockets, and on the edge or open end of the filter pockets, such that when the drawstring is pulled and closes the filter pocket, two radio-opaque markers change distance relative to each other, indicating that an open filter pocket has been closed.

Reference is now made to FIGS. 11A thru 11D, which are schematic illustrations of alternative frame support structures, denoted SF-11A thru SF-11D, respectively, for an embolic protection device. Several alternatives for frame support structures, as at SF-11A, SF-11B, SF-11C, and SF-11D, are shown. A long dimension, denoted L in FIG. 11D, and a short dimension, denoted W in FIG. 11D, both measured in the expanded configuration. For example, when situating an embolic protection device to an aorta the values of L may be in a range from 3 to 50 centimeters and W may be in the range from 10 to 60 millimeters. For example, the frame support structure may support the porous deflector screen, the connecting and the emboli collector portions of the embolic protection device. For example, in some embodiments the entire frame is made of one continuous material, with varying physical dimensions to match the mechanical needs of locating the porous deflector screen over the arterial exits from the aortic arch, and an emboli collector downstream. For example, the connecting portion comprises a frame to provide further force in locating the porous deflector screen to cover the aortic arch arterial exits. FIGS. 11A thru 11D are different embodiments of support frames, each with a porous deflector screen, connector, and emboli collector, but embodiments of other shapes and designs may exist or be developed in the future.

The screen and pockets are not shown in FIGS. 11A thru 11D. The frames are in an unbiased shape, cylindrical, and ready to be rolled into a collapsed configuration. When the device is in the expanded configuration, the porous deflector screen may cover between 20 and 360 degrees of the aortic arch lumen around the exiting arteries (along the circumference of a radial cross section of the aortic arch). The connecting portion may be thinner than the screen, and may cover between 5 and 270 degrees of the descending aorta lumen. The emboli collector cover at least some of the descending aorta, with a bias for covering up to 360 degrees to prevent emboli recirculation.

Some potential advantages of example embodiments of the invention are now specifically pointed out:

In embodiments involving a TAVI/TAVR and/or other trans-catheter procedures through the aorta, wires, and/or a valve delivery system, and/or pigtail catheters, and/or a valvuloplasty balloon pass through the intra-aortic emboli protection filter device at a relatively great distance from the aortic arch and valve, and potentially provide less obstruction and more freedom of movement to the wires, and/or valve delivery system and/or pigtail catheters and/or a valvuloplasty balloon, by not being at a location close to the aortic valve and even not in the aortic arch.

The large size of the emboli collector of the intra-aortic emboli protection filter device potentially provides a good anchor for the filtering device and spreads radial force pressure on the walls of the descending aorta.

The form-fitting area of the porous deflector screen of the intra-aortic emboli protection filter device potentially provides a good anchor for the device and spreads radial force pressure on the walls of the aortic arch.

It is expected that during the life of a patent maturing from this application many relevant filter materials will be developed and the scope of the term filter is intended to include all such new technologies a priori.

It is expected that during the life of a patent maturing from this application many relevant strut materials will be developed and the scope of the term strut is intended to include all such new technologies a priori.

It is expected that during the life of a patent maturing from this application many relevant radio-opaque materials will be developed and the scope of the terms radio-opaque and radio opaque marker are intended to include all such new technologies a priori.

It is expected that during the life of a patent maturing from this application many relevant surgical cardiac procedures will be developed and the scope of the term surgical cardiac procedure is intended to include all such new technologies a priori.

As used herein the term "about" refers to ±10%.

The terms "comprising", "including", "having" and their conjugates mean "including but not limited to".

The term "consisting of" is intended to mean "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a unit" or "at least one unit" may include a plurality of units, including combinations thereof.

The words "example" and "exemplary" are used herein to mean "serving as an example, instance or illustration". Any embodiment described as an "example or "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An embolic protection device comprising: a porous deflector screen comprising a filter shaped as a curved cylinder portion when the embolic protection device is in an expanded configuration, wherein the porous deflector screen is configured to expand and to conform to a wall of a aortic arch, covering entrances to arteries branching from the aortic arch; an emboli collector shaped as a cylinder when the embolic protection device is in the expanded configuration, wherein the emboli collector is configured to expand and to lie along walls of a descending aorta, pushing against walls of the descending aorta and anchoring the porous deflector screen, wherein the emboli collector comprises at least one elongated filter pocket having an opening directed towards the porous deflector screen, wherein: a concavity of the at least one elongated filter pocket is directed opposite to the opening, and when the embolic protection device is in as the expanded configuration, the at least one elongated filter pocket spans at least partway a cylindrical volume, with a length of the at least one elongated filter pocket being along a height of the cylindrical volume, wherein the at least one elongated filter pocket comprises a plurality of elongated filter pockets disposed in parallel; and a connecting portion for connecting the porous deflector screen and the emboli collector, configured to push the porous deflector screen against a superior wall of the aortic arch while anchoring against the emboli collector.

2. The device according to claim 1 in which the porous deflector screen comprises an expandable frame.

3. The device according to claim 1 in which the emboli collector comprises a filter.

4. The device according to claim 1 in which the emboli collector comprises a filter sized to expand and to lie along walls of the descending aorta, the filter comprising holes designed to filter blood through and block emboli.

5. The device according to claim 1 in which the connecting portion is longer than 2 centimeters.

6. The device according to claim 1 in which the connecting portion is longer than 7 centimeters.

7. The device according to claim 1 in which the connecting portion is shaped to expand to a shape of a curved cylinder portion.

8. The device according to claim 1 in which the emboli collector is shaped to expand to a cylindrical shape.

9. The device according to claim 1 in which the at least one elongated filter pocket comprises a frame at an edge of the opening.

10. The device according to claim 1 in which the device comprises at least one radio-opaque marker attached to at least one of: the opening, the porous deflector screen, the emboli collector, and the connecting portion.

11. The device according to claim 1 in which the at least one elongated filter pocket comprises a mechanism for closing the opening.

12. The device according to claim 1 and further including radio-opaque markers for distinguishing when the at least one elongated filter pocket is open and when the at least one elongated filter pocket is closed.

13. The device according to claim 1 in which the emboli collector is structured to overlap by at least 10% of a circumference of the descending aorta.

14. A method for protecting a patient against flow of emboli from an aorta to branching arteries, the method comprising: (a) providing a device comprising: a porous deflector screen comprising a filter shaped as a curved cylinder portion when the embolic protection device is in an expanded configuration, wherein the porous deflector screen is configured to expand and to conform to a wall of a aortic arch, covering entrances to arteries branching from the aorta, an emboli collector shaped as a cylinder when the embolic protection device is in the expanded configuration, wherein the emboli collector is configured to expand and to lie along walls of a descending aorta, pushing against walls of the descending aorta and anchoring the porous deflector screen, wherein the emboli collector comprises at least one elongated filter pocket having an opening directed towards the porous deflector screen, wherein: a concavity of the at least one elongated filter pocket is directed opposite to the opening, and when the embolic protection device is in the expanded configuration, the at least one elongated filter pocket spans at least partway a cylindrical volume, with a length of the at least one elongated filter pocket being along a height of the cylindrical volume, wherein the at least one elongated filter pocket comprises a plurality of elongated filter pockets disposed in parallel and a connecting portion for connecting the porous deflector screen and the emboli collector, configured to push the porous deflector screen against a superior wall of the aortic arch while anchoring against the emboli collector; (b) inserting the device via a catheter into the aorta, such that: said porous deflector screen is placed at the aortic arch, the filter of the porous deflector screen blocking exits to arteries branching off the aortic arch; said emboli collector is placed at the descending aorta and unfurled so a surface lies along walls of the descending aorta.

15. The method according to claim 14 further comprising using the catheter to remove the device from the aorta.

16. The method according to claim 14 further comprising closing the opening of the at least one elongated filter pocket by pulling a cord for drawing closed the opening prior to removing the device from the aorta.

17. The method according to claim 14 further comprising performing a procedure on a heart of the patient by passing a surgical tool through the emboli collector of the device, next to the at least one elongate filter pocket.

18. The method according to claim 14 further comprising performing a procedure on a heart of the patient by passing a surgical tool through the emboli collector of the device, between the plurality of elongated filter pockets.

19. The method according to claim 14 further comprising, following the inserting, performing an on-pump cardiac operation on a heart of the patient.

* * * * *